United States Patent
Pryor

(10) Patent No.: US 8,306,635 B2
(45) Date of Patent: Nov. 6, 2012

(54) MOTIVATION AND ENHANCEMENT OF PHYSICAL AND MENTAL EXERCISE, REHABILITATION, HEALTH AND SOCIAL INTERACTION

(75) Inventor: Timothy Pryor, Windsor (CA)

(73) Assignee: Motion Games, LLC, Austin, TX (US)

( * ) Notice: Subject to any disclaimer, the term of this patent is extended or adjusted under 35 U.S.C. 154(b) by 850 days.

(21) Appl. No.: 12/358,404

(22) Filed: Jan. 23, 2009

(65) Prior Publication Data
US 2009/0233769 A1 Sep. 17, 2009

Related U.S. Application Data

(63) Continuation of application No. 11/832,134, filed on Aug. 1, 2007, and a continuation-in-part of application No. 11/980,717, filed on Oct. 31, 2007, now Pat. No. 7,693,584, which is a continuation of application No. 11/118,774, filed on May 2, 2005, now Pat. No. 7,328,119, which is a continuation-in-part of application No. 09/799,797, filed on Mar. 7, 2001, now abandoned.

(60) Provisional application No. 61/022,991, filed on Jan. 23, 2008.

(51) Int. Cl.
| | |
|---|---|
| *G05B 11/01* | (2006.01) |
| *G05B 15/00* | (2006.01) |
| *G06F 3/00* | (2006.01) |
| *G06F 3/048* | (2006.01) |
| *A63B 71/00* | (2006.01) |

(52) U.S. Cl. ............ 700/17; 700/83; 715/744; 715/745; 715/788; 715/789; 715/810; 715/811; 482/5; 482/8

(58) Field of Classification Search .................... 700/17, 700/83; 715/700, 744–745, 781, 788–789, 715/810–811; 482/5, 8
See application file for complete search history.

(56) References Cited

U.S. PATENT DOCUMENTS

| | | |
|---|---|---|
| 3,846,826 A | 11/1974 | Mueller |
| 4,014,000 A | 3/1977 | Uno et al. |
| 4,146,924 A | 3/1979 | Birk et al. |
| 4,199,137 A | 4/1980 | Giguere |
| 4,219,847 A | 8/1980 | Pinkney et al. |

(Continued)

FOREIGN PATENT DOCUMENTS

JP 63167923 7/1988

OTHER PUBLICATIONS

Wo 93/05711; 35 pages; Publication Date of Jan. 4, 1993; Jan Lepley.*

(Continued)

*Primary Examiner* — Ronald Hartman, Jr.
(74) *Attorney, Agent, or Firm* — Warner Norcross & Judd LLP

(57) ABSTRACT

The disclosed invention primarily relates to methods for assisting and motivating persons with respect to various exercise and rehabilitation regimens they might undertake, mentally as well as physically. The invention also has potential application to for diagnosis and/or treatment of certain mental and physical disorders, and in other situations where a form of companionship may be provided the user. In addition the invention herein provides an enjoyable means of social interaction with others providing further motivation for physical and mental activity represented.

23 Claims, 13 Drawing Sheets

U.S. PATENT DOCUMENTS

| | | | | |
|---|---|---|---|---|
| 4,305,131 | A | 12/1981 | Best | |
| 4,375,674 | A | 3/1983 | Thornton | |
| 4,396,945 | A | 8/1983 | DiMatteo et al. | |
| 4,408,613 | A | 10/1983 | Relyea | |
| 4,416,924 | A | 11/1983 | Peterson et al. | |
| 4,435,835 | A | 3/1984 | Sakow et al. | |
| 4,475,122 | A | 10/1984 | Green | |
| 4,484,179 | A | 11/1984 | Kasday | |
| 4,542,375 | A | 9/1985 | Alles et al. | |
| 4,602,280 | A | 7/1986 | Maloomian | |
| 4,613,942 | A | 9/1986 | Chen | |
| 4,629,319 | A | 12/1986 | Clarke et al. | |
| 4,631,676 | A | 12/1986 | Pugh | |
| 4,631,847 | A | 12/1986 | Colin | |
| 4,654,872 | A | 3/1987 | Hisano et al. | |
| 4,654,949 | A | 4/1987 | Pryor | |
| 4,672,564 | A | 6/1987 | Egli et al. | |
| 4,686,374 | A | 8/1987 | Liptay-Wagner et al. | |
| 4,687,200 | A | 8/1987 | Shirai | |
| 4,751,642 | A | 6/1988 | Silva et al. | |
| 4,843,568 | A * | 6/1989 | Krueger et al. | 382/100 |
| 4,988,981 | A | 1/1991 | Zimmerman et al. | |
| 5,072,294 | A | 12/1991 | Engle | |
| 5,148,591 | A | 9/1992 | Pryor | |
| 5,168,531 | A | 12/1992 | Sigel | |
| 5,277,678 | A * | 1/1994 | Friedebach et al. | 482/70 |
| 5,297,061 | A | 3/1994 | Dementhon et al. | |
| 5,325,472 | A | 6/1994 | Horiuchi et al. | |
| 5,388,059 | A | 2/1995 | DeMenthon | |
| 5,423,554 | A | 6/1995 | Davis | |
| 5,454,043 | A | 9/1995 | Freeman | |
| 5,459,793 | A | 10/1995 | Naoi et al. | |
| 5,489,249 | A * | 2/1996 | Brewer et al. | 482/5 |
| 5,506,682 | A | 4/1996 | Pryor | |
| 5,521,616 | A | 5/1996 | Capper et al. | |
| 5,524,637 | A * | 6/1996 | Erickson | 600/592 |
| 5,527,239 | A * | 6/1996 | Abbondanza | 482/8 |
| 5,566,283 | A | 10/1996 | Modegi et al. | |
| 5,577,981 | A * | 11/1996 | Jarvik | 482/4 |
| 5,581,276 | A | 12/1996 | Cipolla et al. | |
| 5,591,104 | A * | 1/1997 | Andrus et al. | 482/7 |
| 5,594,469 | A | 1/1997 | Freeman et al. | |
| 5,616,078 | A * | 4/1997 | Oh | 463/8 |
| 5,617,312 | A | 4/1997 | Iura et al. | |
| 5,624,117 | A | 4/1997 | Ohkubo et al. | |
| 5,645,513 | A * | 7/1997 | Haydocy et al. | 482/57 |
| 5,704,836 | A * | 1/1998 | Norton et al. | 463/36 |
| 5,772,522 | A | 6/1998 | Nesbit et al. | |
| 5,800,314 | A * | 9/1998 | Sakakibara et al. | 482/54 |
| 5,850,352 | A * | 12/1998 | Moezzi et al. | 345/419 |
| 5,870,771 | A | 2/1999 | Oberg | |
| 5,878,174 | A | 3/1999 | Stewart et al. | |
| 5,889,505 | A | 3/1999 | Toyama et al. | |
| 5,890,262 | A * | 4/1999 | Orozco | 16/239 |
| 5,913,727 | A | 6/1999 | Ahdoot | |
| 5,926,168 | A | 7/1999 | Fan | |
| 5,966,310 | A | 10/1999 | Maeda et al. | |
| 5,982,352 | A | 11/1999 | Pryor | |
| 6,004,243 | A * | 12/1999 | Ewert | 482/8 |
| 6,005,548 | A | 12/1999 | Latypov et al. | |
| 6,008,800 | A * | 12/1999 | Pryor | 345/173 |
| 6,030,290 | A | 2/2000 | Powell | |
| 6,043,805 | A | 3/2000 | Hsieh | |
| 6,049,327 | A | 4/2000 | Walker et al. | |
| 6,057,856 | A | 5/2000 | Miyashita et al. | |
| 6,084,979 | A | 7/2000 | Kanade et al. | |
| 6,097,369 | A | 8/2000 | Wambach | |
| 6,098,458 | A | 8/2000 | French et al. | |
| 6,147,678 | A | 11/2000 | Kumar et al. | |
| 6,152,856 | A * | 11/2000 | Studor et al. | 482/8 |
| 6,179,746 | B1 * | 1/2001 | Delman | 482/6 |
| 6,198,485 | B1 | 3/2001 | Mack et al. | |
| 6,198,487 | B1 | 3/2001 | Fortenbery et al. | |
| 6,220,865 | B1 | 4/2001 | Macri et al. | |
| 6,227,974 | B1 | 5/2001 | Eilat et al. | |
| 6,308,565 | B1 | 10/2001 | French et al. | |
| 6,336,891 | B1 * | 1/2002 | Fedrigon et al. | 482/8 |
| 6,342,917 | B1 | 1/2002 | Amenta | |
| 6,346,929 | B1 | 2/2002 | Fukushima et al. | |
| 6,358,188 | B1 | 3/2002 | Ben-Yehuda et al. | |
| 6,428,449 | B1 * | 8/2002 | Apseloff | 482/3 |
| 6,430,997 | B1 | 8/2002 | French et al. | |
| 6,453,180 | B1 | 9/2002 | Endoh et al. | |
| 6,471,586 | B1 * | 10/2002 | Aiki et al. | 463/6 |
| 6,597,817 | B1 | 7/2003 | Silverbrook | |
| 6,677,967 | B2 | 1/2004 | Sawano et al. | |
| 6,682,351 | B1 * | 1/2004 | Abraham-Fuchs et al. | 434/247 |
| 6,712,692 | B2 * | 3/2004 | Basson et al. | 463/7 |
| 6,720,949 | B1 * | 4/2004 | Pryor et al. | 345/158 |
| 6,727,887 | B1 | 4/2004 | Levine et al. | |
| 6,750,848 | B1 | 6/2004 | Pryor | |
| 6,766,036 | B1 * | 7/2004 | Pryor | 382/103 |
| 6,766,063 | B2 | 7/2004 | Gonsalves | |
| 6,921,332 | B2 | 7/2005 | Fukunaga et al. | |
| 6,954,906 | B1 | 10/2005 | Kamachi et al. | |
| 7,015,950 | B1 | 3/2006 | Pryor | |
| 7,038,855 | B2 * | 5/2006 | French et al. | 359/630 |
| 7,098,981 | B2 * | 8/2006 | Nakayoshi et al. | 349/141 |
| 7,359,121 | B2 * | 4/2008 | French et al. | 359/630 |
| 7,401,783 | B2 * | 7/2008 | Pryor | 273/237 |
| 7,627,139 | B2 * | 12/2009 | Marks et al. | 382/103 |
| 7,843,429 | B2 * | 11/2010 | Pryor | 345/158 |
| 8,012,107 | B2 * | 9/2011 | Einav et al. | 601/5 |
| 2001/0021665 | A1 * | 9/2001 | Gouji et al. | 463/7 |
| 2002/0022551 | A1 * | 2/2002 | Watterson et al. | 482/8 |
| 2002/0036617 | A1 * | 3/2002 | Pryor | 345/156 |
| 2002/0055418 | A1 * | 5/2002 | Pyles et al. | 482/8 |
| 2003/0214530 | A1 * | 11/2003 | Wang et al. | 345/757 |
| 2004/0063480 | A1 | 4/2004 | Wang | |
| 2004/0087366 | A1 * | 5/2004 | Shum et al. | 463/36 |
| 2005/0064936 | A1 | 3/2005 | Pryor | |
| 2005/0179202 | A1 * | 8/2005 | French et al. | 273/247 |
| 2006/0033713 | A1 | 2/2006 | Pryor | |
| 2006/0202953 | A1 | 9/2006 | Pryor et al. | |
| 2007/0021199 | A1 * | 1/2007 | Ahdoot | 463/30 |
| 2007/0219059 | A1 * | 9/2007 | Schwartz et al. | 482/8 |
| 2010/0162177 | A1 * | 6/2010 | Eves et al. | 715/863 |
| 2010/0190610 | A1 * | 7/2010 | Pryor et al. | 482/8 |
| 2010/0197462 | A1 * | 8/2010 | Piane, Jr. | 482/5 |
| 2010/0246898 | A1 * | 9/2010 | Izumi | 382/106 |
| 2010/0295783 | A1 * | 11/2010 | El Dokor et al. | 345/158 |
| 2011/0034300 | A1 * | 2/2011 | Hall | 482/1 |

OTHER PUBLICATIONS

Bales et al, "Marking Parts to Aid Robot Vision", NASA Technical Paper 1819, Apr. 1981.

* cited by examiner

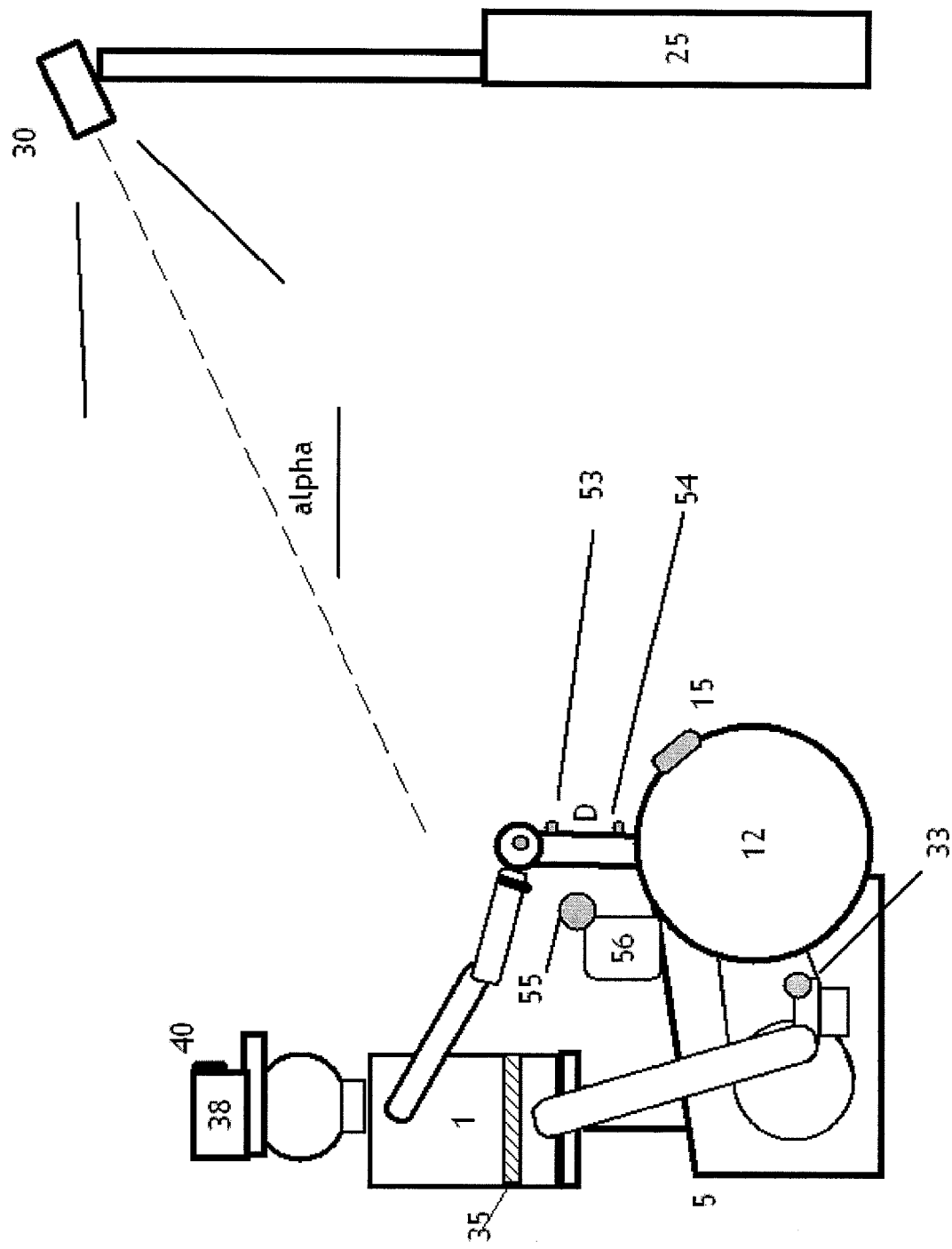

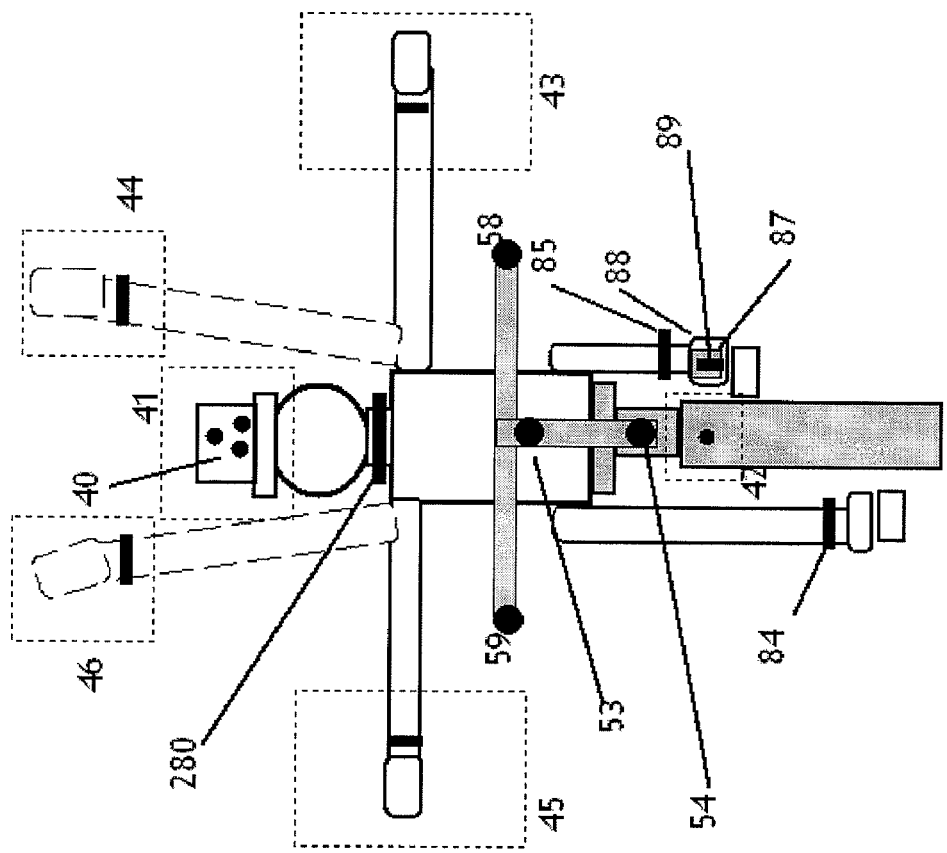
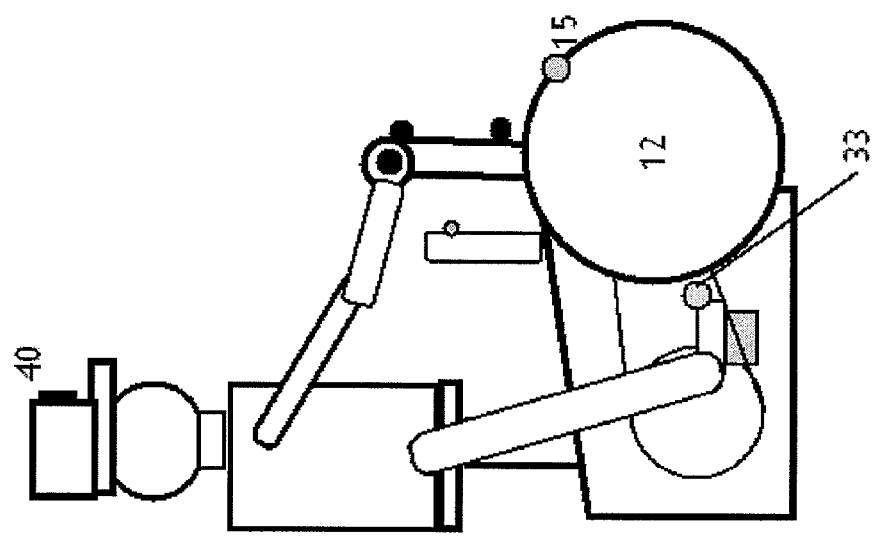
figure 1 c

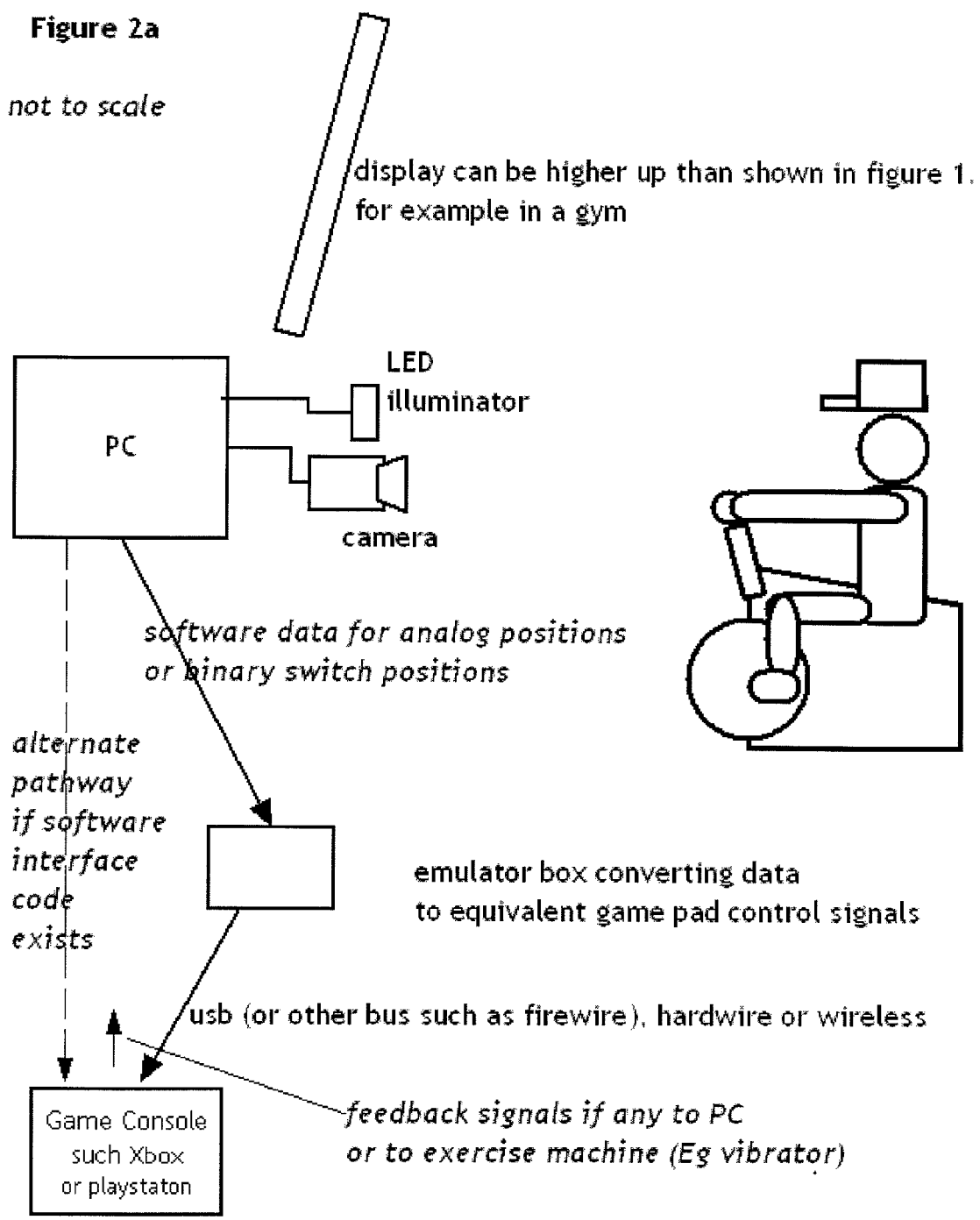

Figure 2b Table of Correspondence between Standard Type Video Game Game pad and Optically sensed position relating to one car chase game example played while on an exercise bike.

| Function in Game | Game Pad Control | Person/Bike Set 1 | Person/Bike Alternate Set 2 |
|---|---|---|---|
| Car turns left | D Pad left button | Left hand moved to fully extended position outward | Leans left, head moves to left and sensed |
| Car turns right | D Pad right button | Right hand moved to fully extended position outward | Leans right, head moves to right and sensed |
| Car speed control | Switch for accelerator | Bike wheel rotation rate sensed from point on wheel | Bike wheel rotation rate sensed from toe of person riding |
| Car brakes | Switch for brake | Brake position on bike | Persons right hand fully extended upwards to slow virtual speed in game, but not actual bike wheel speed. |
| Car shoots rocket | Trigger button | | Person punches hand straight forward |
| Handicap | Via Button clicks on one of buttons | Setting of resistance lever or other control | Voice entered via dragondictate |
| | | | |

Note that in both set 1 and 2 the head orientation can be sensed independently, allowing the view point on the screen to be changed accordingly in the program

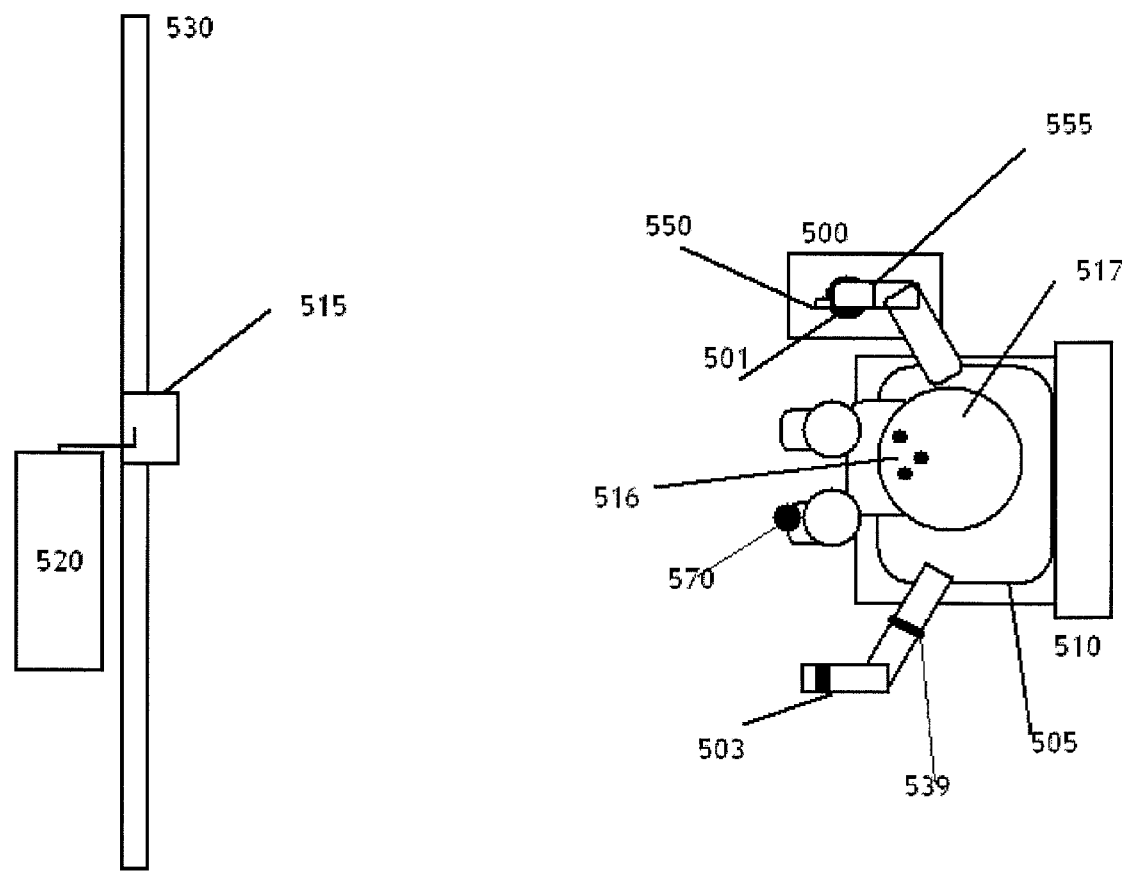

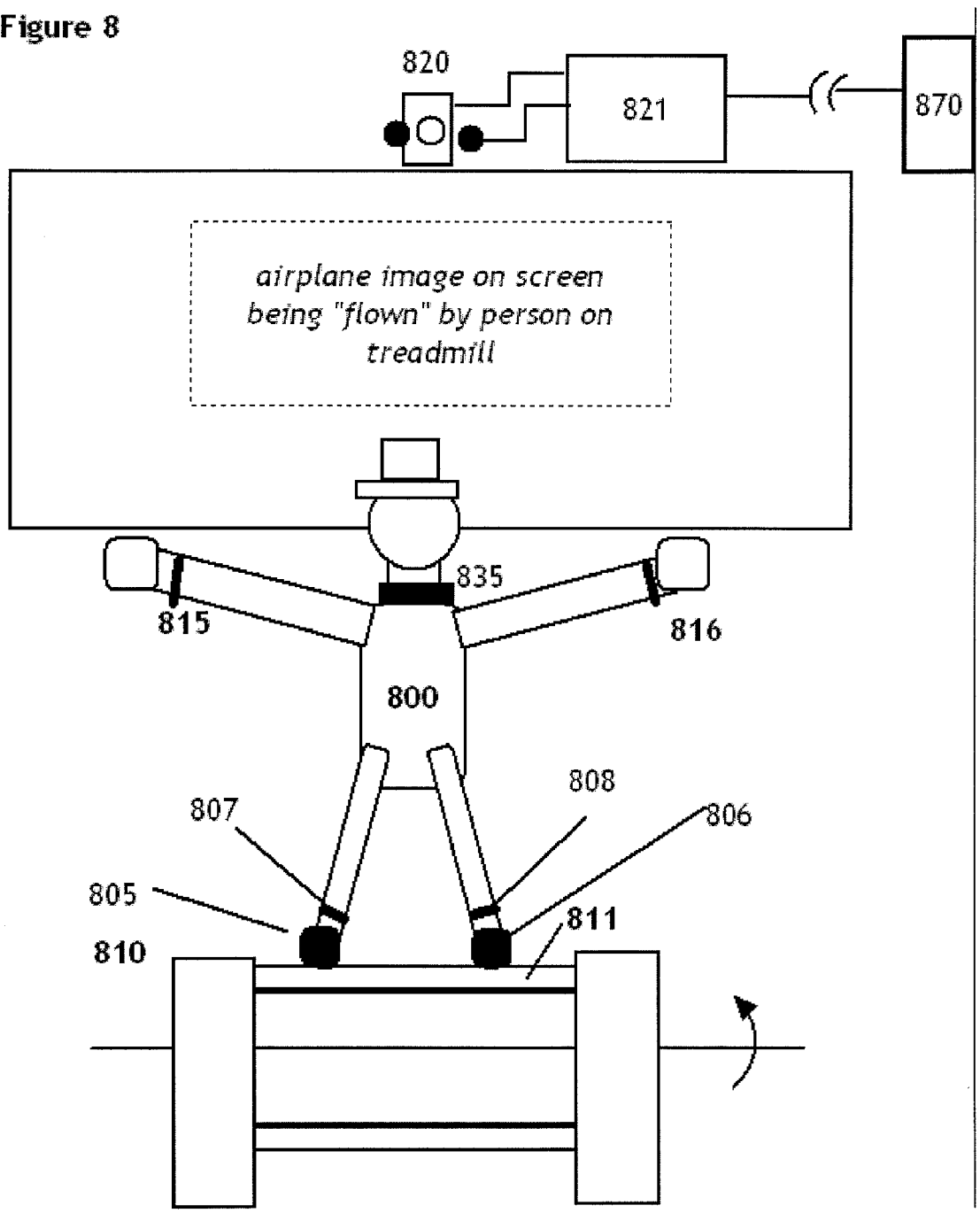

MOTIVATION AND ENHANCEMENT OF PHYSICAL AND MENTAL EXERCISE, REHABILITATION, HEALTH AND SOCIAL INTERACTION

CROSS REFERENCE TO RELATED APPLICATIONS

Benefit is claimed of U.S. provisional application 61/022,991, filed Jan. 23, 2008 "Motivation and Enhancement of Physical and Mental Exercise, Rehabilitation and Health"; which is herein incorporated by reference. This application claims benefit of provisional application 61/022,991, filed Jan. 23, 2008 and entitled "Motivation and Enhancement of Physical and Mental Exercise, Rehabilitation and Health"; which is herein incorporated by reference.

This application is a continuation of Ser. No. 11/832,134 filed Aug. 1, 2007 entitled "Reconfigurable Tactile Control Display Applications". This application is also a continuation in part of U.S. Ser. No. 11/980,717 entitled "Camera Based Video Games and Related Methods for Exercise Motivation" filed Oct. 31, 2007 now U.S. Pat. No. 7,693,584; which is a continuation of Ser. No. 11/118,774 filed May 2, 2005, now U.S. Pat. No. 7,328,119; which is a continuation in part of Ser. No. 09/799,797 filed Mar. 7, 2001, now abandoned. Benefit to all of these earlier applications is claimed, and they are hereby incorporated by reference.

The invention is related to several of my previous and in some cases copending applications, such as Ser. No. 10/934,762; Ser. No. 11/429,305; U.S. Pat. No. 6,766,036; U.S. Pat. No. 6,750,848; U.S. Pat. No. 7,015,950; U.S. Ser. No. 11/186,898, the disclosures of which are incorporated by reference herein. These disclosures illustrate method and apparatus for determining features on objects and persons which can be used for entertainment and gaming, as well as more serious purposes such as weight loss, physical rehabilitation, diagnosis of illnesses and the like.

FIELD OF THE INVENTION

The invention is generally in the field of exercise related equipment and systems, particularly those using at least in part, one or more electro-optical sensors such as a TV camera to determine actions of a user and/or equipment such as exercise machines which in turn may control or otherwise be inputted to a program for the purposes of gaming, physical rehabilitation, assessment, diagnostics, training, health maintenance purposes and the like. The principal applications are entertainment and physical and/or mental health related, separately or in combination.

BACKGROUND OF THE INVENTION

A well known health care problem relates to the lack of motivation of persons wishing, or needing, to undertake exercise or rehabilitation therapy. They therefore do not undertake the desired treatment steps to maintain wellness or to return to the workplace. The result is an enormous burden on the public as well as on the persons own well being. For example the Governor of Michigan in November 2007 in a speech to the Governors Fitness Council obesity related issues alone were costing the state 12 billion dollars per year. This is due to direct medical costs and lost work time. Additional costs also relate to persons undertaking such activity in a manner that does not achieve the desired effect. For example, short changing a regimen prescribed to make ones wrist heal from carpal tunnel damage. Doing ones exercises right is a big problem too, and recovery can be impeded if not done well.

Another aspect is mental health, which often can be present along with physical health problems or lead to same. Physical activity can be helpful for mentally ill persons, especially those on antipsychotic drugs that cause weight gain. Here too a motivation is needed, indeed doubly so one might argue.

Finally because of the popularity of video games, it may be possible to use these not only to provide the motivation, but also to provide the means to take data which can be used to guide therapy and provide diagnosis Several of these concepts have been disclosed in my related co-pending applications. Recently Nintendo company has been extremely successful in commercializing a very nicely thought out device, the Wii, that takes one step toward providing the requisite motivation. The Wii however, lacks a crucial element, namely the ability to see points on you, or an exercise machine or object you are working with. In addition, it can be tricked by using small movements to stand in for big ones. Since it doesn't in many cases monitor position or motion directly, it can't advise you in real time or otherwise if your movement is correct, or needs correction. And it cannot accumulate data on your activity that would be desirable for medical or other purposes.

SUMMARY OF THE INVENTION

The invention herein discloses simple, robust and affordable methods and apparatus to motivate people to do exercise either on exercise machines or in free space, while accumulating data on their movements as desired for medical or other purposes. One or more 2-D or 3-D cameras obtain data from various portions of a person and/or exercise machine or other exercise related object. This data relating to positions orientations and movements of these portions is in a preferred embodiment used as an input to a video game, replacing in whole or in part, the input controls of the standard button type or other game controller for which the game was initially designed. The player then can by moving his or her limbs, or a machine apparatus, engage in exercise while playing a game that would be of interest. This then provides motivation to undertake the exercise, and special game programs or subprograms for this purpose, or for diagnostic purposes may also be created as will be disclosed.

Another purpose of the invention is to enable the simultaneous accumulation of data concerning the exercise or therapeutic movement activity. The data may also be used to create the enhanced gaming graphics or other gaming and social activities and opportunities offered by the invention and for potentially diagnosing of both mental and physical disorders such as movement disorders and social disorders. A third and related aspect of the invention is to provide new opportunities for therapy for such disorders, and in a way that could increase the chances of the person undertaking therapy.

It is also a goal of the invention to provide method and apparatus to enable persons to undertake further and better exercise than they normally would, as a result of increased motivation and other factors. This is particularly the case with exercise involving other wise boring exercise machines which however are often the very ones needed to allow serious weight loss and/or rehabilitation of injuries. At the same time the invention allows them to undertake such activity with reduced risk of overexertion or strain.

It is a goal of the invention to provide improved methods of physical or occupational rehabilitation therapy, while at the same time increasing the effectiveness of home treatment and providing information for physical or occupational therapists to indicate movement in a given angle or dimension, the number of repetitions and rate achieved by a consumer, and the progress made while further motivating and informing the consumer.

It is a goal of the invention to provide low cost computer and electro-optical means for determining positions and movements of persons and machines at multiple points at rates sufficient to determine the information desired for a particular game or exercise, and to display needed information, goals, historical data and other information of use to the person on a display, which in many cases may already be present for TV watching or the like.

It is a goal of the invention to provide a method and apparatus useable on a plurality of different types of exercise machines in order to for example allow the same game to be played using each machine, but perhaps using different machine features or human portions as the input to the game It is a further goal of the invention to provide a means for disabled persons, including those in wheelchairs, to play entertaining games which further may provide helpful exercise of upper body and other portions.

It is an additional goal of the invention to provide methods to assist in the treatment of mental, behavioral, or other disorders and in situations where a form of companionship may be provided the user, including remote real or virtual companions using the Internet or other means.

It is a goal of the invention to provide a method for directly determining a persons positions, orientations or movements for exercise related activity which allows limits or guidelines to be set which can be accurately monitored to see if criteria are achieved.

And it is also a goal of the invention to provide a method for directly determining a persons positions, orientations or movements for exercise related activity which allows limits or guidelines to be set which can be accurately monitored to see if criteria are achieved or for internet multi-person activity especially in addition it makes up for a general deficiency of Nintendo Wii which doesn't give actual positions of a person and thus while encouraging exercise, it doesn't really answer needs of many who need help.

It is a further goal of the invention to assist a user to optimize their performance of exercise or other activity using data feedback from points determined by the invention, as well as optional information such as heart rate, oxygen, etc.

It is another goal of the invention to provide a method and apparatus useable on a plurality of exercise machines simultaneously for both sensing of persons and objects used as well as to have multiple person games It is also a goal of the invention to provide method and apparatus utilizing natural or artificial features on a person or their clothing, to enable their positions and movements to be entered into the computer from which their activity may be calculated It is also a goal of the invention to provide method and apparatus for providing datum's on exercise machines to enable their positions and movements to be entered into the computer, to calculate activity of a person using them.

It is a further goal of the invention to provide method and apparatus for determining motion of persons and calculate caloric burn rate there from, which data can be transmitted over the internet to health providers or others if desired, along with other data such as degree of arm extension, ankle rotation and the like It is a goal of the invention to provide for means to control an avatar of themselves or someone in a social networking site or other venue and where desired to incorporate this function into a game involving exercise.

It is a goal of the invention to provide life size stand up screen for use when exercising to visualize computer graphics, or others socially interacting with you. The screen may also be used for normal HDTV by turning it sideways.

It is a goal of the invention to provide games involving ordinary exercise machines such as bicycles, treadmills, elliptical machines and the like which can both monitor machine locations as well as locations on the person using them in order to effect the game.

It is also a goal of the invention to predict the effect on ones appearance (clothed, or even unclothed) of future activity such as diet or exercise and to allow one to iterate the prediction, such that a user can optimally tradeoff, the various factors such as caloric intake, exercise time and the like, with the appearance predicted to result from same.

It is a goal of the invention to affect a method for social interaction for example over the internet while undertaking games of the invention.

It is another goal the invention to provide simple means by which conventional game consoles or game computers can be adapted for use with the invention herein.

It is also a goal to provide simplified machine vision processing means which can be optimized for the game to be played and/or the exercise machine to be used.

It is a further goal of the invention to provide methods for calibrating systems with respect to the sensor and display device, in consideration of the game or other program requirements.

It is another goal of the invention to provide simplified methods of setting up the system with different exercise equipment and in different locales.

Further features and advantages of the present invention will be set forth in, or apparent from, the detailed description of preferred embodiments thereof which follows.

BRIEF DESCRIPTION OF THE DRAWINGS

FIG. 1b illustrates a side view of the bicycle of FIG. 1a, further including a person (also called rider, or player in this document) riding the bike.

FIG. 1c illustrates simplified image processing aspects

FIG. 2a illustrates one method of utilizing commercial video games running on game consoles or PCs FIG. 2b is an illustrative correlation table of positions for two alternate ways to play a certain classical video game while exercising on an exercise machine.

FIG. 5 illustrates a simple device used by a senior citizen seated in a chair, or persons in wheel chairs, which uses head or upper body motions.

FIG. 8 illustrates an airplane game embodiment on a treadmill

DESCRIPTION OF THE PREFERRED EMBODIMENTS

Figure 1A:
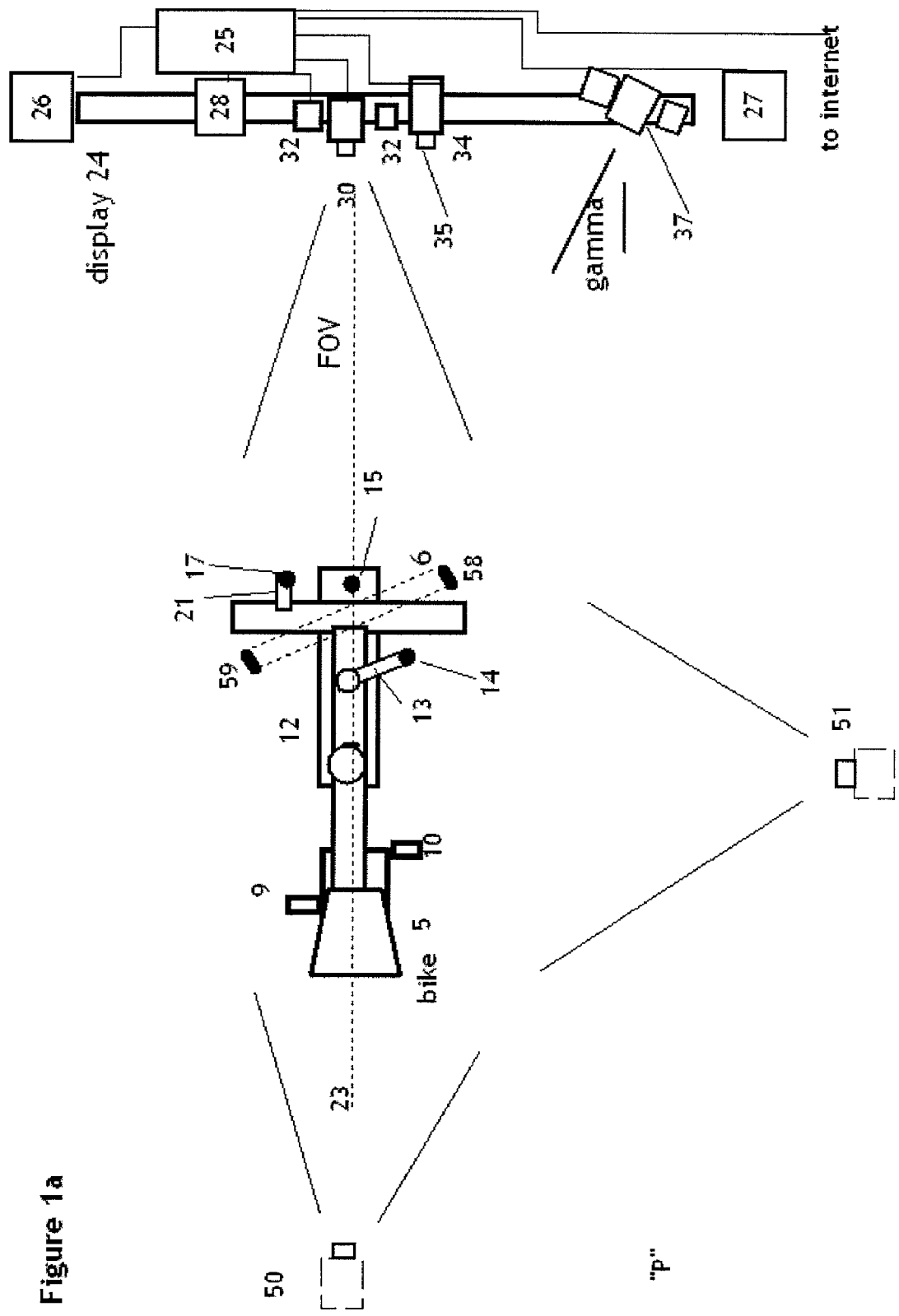
FIG. 1a illustrates a top view of an exercise bicycle embodiment.

FIG. 1a illustrates an exercise bicycle embodiment the invention. This has been mentioned in other of my patent applications, and is here discussed in some detail. There are basically two kinds of indoor bikes that are presently used for exercise-a stationary exercise bike and a sort of road bike, which allows you to simulate riding down the road. In these latter cases are also training devices that are used to allow you to bring your own road bicycle into your family room so to speak and write it there by having rollers allow the wheels to move without going anywhere. This discussion is mainly going to focus on the use of a classical stationary exercise bike but it is understood that the invention applies to other bikes, and a large gamut of other exercise equipment which the user moves against a resistance with either his hands or feet or both.

The invention may be used monitor the position of one or both pedals, a member moving with them, or the feet (or ankles or legs) of a user and thus by measuring the motion determine the rate at which the wheel is being turned by the user. Other exercise machine related variables like a degree of resistance (also called tension) dialed in can be monitored if the movement such as a lever position to execute changes in resistance can be seen by a camera or other electro-optical sensor of the invention. Similarly other features may also be so monitored with the sensor, such as optional features added such as game control levers or buttons. Location of any steer able handlebar present can also be determined. If desired the position of the rider in terms of seat or handlebar height can also be measured. Person variables can also be monitored such as head location and orientation, tilt (lean) of the person to one side or other, hand position, arm state (straight, bent) neck location, waist location feet location, knee location and other variables if desired.

As shown in FIG. 1a is a top view of a stationary exercise bike 5, such as a Schwinn spinning type having handlebars 6 and pedals 9 and 10 used to drive wheel 12, via a chain or belt drive. A brake lever 13 and a optional added game lever or button 14 are also shown. Movable portions of the bike such as pedals, levers and in some cases handle bars may be provided, In a preferred embodiment location and/or movement and in some cases orientation of contrasting portions are sensed using at least one camera such as 30. Such contrasting portions may be for example retroreflector targets such as target 15 on wheel 12, target 16 on brake 13, target 17 on lever 21, and target 18 on a turn able knob 19 that is used by the rider to control resistance against the wheel, and thus effort to turn the wheel A video display 24 typically a large screen LCD or plasma display or projection display is located ahead of the person, which display is typically 60 inches diagonal with a horizontal extension of about 52 inches. It can be a very large screen such as 120 inch diagonal projected on a wall. Generally speaking, I have found that more the images on the screen approach life-size, in relation at least to the player, the more interesting the game is. As shown previously it is possible to turn a HDTV 16:9 format TV to have its long axis vertical, in order that a person seen on the TV are more life size appearing in relation to the rider and bike. This is very realistic for social activities and a more realistic feeling to the social interaction is made possible as is described below. For example a 53 inch high screen of the above 61 inch diagonal example is about the size desirable for bike rider to bike rider interaction such as described in FIG. 6. A PC 25 controls the display 24, as well as two speakers 26 and 27, and a microphone 28.

PC 25 can be used as well to process images of camera 30 using machine vision algorithms known in the art (for example the MIL software library of Matrox corporation in Montreal, Quebec) in order to identify and determine where points such as those on the machine or the person exercising are located in the image field. Using this data, and potentially data from sequential image frames, the computer 25 can determine one or more variables relating to a particular point in question, such as its position, position relative to another point, velocity, acceleration and direction of motion. Alternatively a second computer other than PC 25 can be used for this image processing and variable determining purpose and in turn interfaced to PC 25. This computer could in another example be resident in the housing of PC 25.

In one embodiment of this application, a single black and white TV camera 30, having a Field of View (FOV) sufficient to see all points on the person and bike required, such as a one megapixel PL A741 Pixel link company model is interfaced to PC 25 via fire wire, USB or other means, and is used to monitor points on the person and points on the bike in order to provide information to the game software, whose images are provided on the display screen 24 via the computer and sounds via speakers 26 and 27. Other black and white cameras or color cameras can be alternatively used even those with only 640×480 pixels. (Which also may achieve higher camera frame rates as a result), This camera 30 is generally equipped with an infrared band pass filter 31 passing the same wavelength as the source (e.g. 820 nm) so as to reject light outside of as narrow a band as possible around this wavelength and thus increase signal to noise. Since good interference filters of this type are expensive, it is often possible to use a simple black appearing plastic that effectively cuts off substantially all visible light, but typically not wavelengths longer than the led. This generally serves to eliminate the effect of florescent lighting or LED lighting, but does not reject all incandescent for example.

In this particular version two near Infrared OSRAM LEDs serve as light source 32 mounted next to the camera which light source in this particular application is been chosen to have a IR radiation at 820 nm and is also controlled by PC 25. IR is used so that the light from the LED is not obtrusive to the user, as it is pointing as shown in the direction of the user's eyes. This goal can alternatively be achieved by providing the user with narrow band (eg 50 nm) filter glasses that block the LED wavelength, if a visible led or other source is used. In this case a LED source of any particular color that can be so blocked can be used. And this in turn allows ordinary color webcams to be used rather than a black and white camera, which could potentially lower the cost. (at a price of typically lower sensitivity and lower resolution—ok for some games)

The purpose of the LED attached to the camera is to illuminate points on the person and the bike, and possibly other associated objects as well. These points are advantageously, but not necessarily comprised by retro reflective targets, though other features can be used if sufficiently visible and recognizable at the speed desired, and generally within the cost constraint of affordable equipment for the customer in question.

An optional color webcam 34 may also be connected to PC 25 for internet image transmission. Room lights are typically used to illuminate objects viewed by the webcam. The TV camera 34 may transmit an image of the person on the bike to a remote location where there is another person exercising, a therapist, or someone else who may wish to interact or record the activity. In a health care related embodiment this webcam (or another located elsewhere) can be turned on automatically in the game if unusual behavior is spotted, by for example comparison of movements or other actions such as voice, with norms for that portion of a game. This ability to provide information of medical value, while allowing a patient to play popular "normal" video games, is a big advantage in addition to the motivation for exercise. It should be noted that even when people are playing a Wii game for example, a separate webcam of this nature can be used to monitor and record or transmit their movement related information. At some point in the future, such data could be combined with the wii software itself to provide added game functions.

To avoid the bright spots from the retro reflective targets, if used (as is often desirable to speed up and render more robust the machine vision processing), webcam 34 is optionally fitted with a band blocking interference filter known in the art 35 to block the wavelength of radiation of IR LED 32 if such is not sufficiently blocked by the Bayer or other filter array employed in the webcam to separate colors.

FIG. 1b illustrates a side view of the bicycle game of FIG. 1a, in this case including the person riding the bike. The person 1 seated on bike 5 is in this example also equipped with retro reflective targets; a target wristband 36 and targeted hat (which can be a sweat band for example) 38 which has a 3 or four target set 40 facing forward toward the camera and light source 30.

Some useful targets and locations for bicycle related or other games or activity are for example shown in the figures below The target 15 on spinning wheel 12 is monitored to determine how many times per minute for example it is seen coming back to the same position by camera 30, thus indicative of the rotational rate of the wheel. One can alternatively use for example a target such as 33 on the person's shoes (eg on a toe as well or alternatively if desired to determine wheel rotation rate). Generally speaking it is desirable to use features that can be seen with the least FOV required of the camera, thus optimizing the camera resolution. Thus looking at wheel rotation marker 15 near the top of the wheel rotation is preferred to looking at the bottom, since generally the hands raised vertically define the FOV in the upper vertical direction (but don't necessarily have to, there could be a game that restricted the complete field to points nearer the handlebars for example. While large cameras are now available, a common 640×480 pixel VGA one is generally satisfactory and preferred as there is less data to transfer and process and one can run faster. As speeds of Buses and chips increase, so may this number. Or the speed of the processing can increase to increase accuracy and reduce blur (see also FIG. 3)

The 3 dot target set is further shown in FIG. 1c and such a set allows head orientation and location in all 6 axes using the single camera 30. The ROI boxes 41 to 46 in FIG. 1c provide one example of the regions of interest which may be processed by computer 25 in the image of camera 30. Box 41 includes the region in which the head target set 40 is expected as part of the exercise game(s) to be played. Box 42 includes the region where the target 15 is expected to pass thru.

ROI Box 43 includes the region where the wrist target 36 on the person's left hand when outstretched to the side, while box 44 is the region when outstretched and raised. Similarly Box 45 includes the region where the wrist target on the persons right hand i when outstretched to the side, while box 46 is the region when raised. The three target set is not near the hand locations as shown, but if confusion results (e.g. in a game with lots of movement required) a simple processing step can distinguish this set from the wrist target shape, which appears like a line in the image. More regions or other regions of the person or bike can be chosen, but this illustrates a sufficient number to conduct a spinning class activity or to play for example, a car chase game It should be further noted that a machine could have a simple retro reflective or other marker related to the amount of resistance one has dialed in, such as a target 55 on knob 56 shown in FIG. 1b. Note we can add other mechanical control functions to the bike (or other machine) buttons, levers which push down against a spring like a gas pedal, handlebar grips which are spring loaded and rotate a target like a motorcycle throttle control, and so forth. In each case the camera is used to acquire the data from them to provide a solution at lowest cost and complexity, though other transduction means could be used and interfaced conventionally to the PC 25 if desired.

If white light is used for sensing purposes, all movable position controls that need to be sensed on the bike might be orange or some other easy to recognize color against background, which ideally would be black such that room light or projected light substantially reflects off the targets only. The camera can see that as well without any sort of additional transducers and their cost, wires and complexity. This same ability to is easily see things also can relate to other types of exercise machines, which also have adjustable resistances or inclines or other things that are changed to increase the amount of work that one must do to of operate the machine.

Some components used in the above embodiments and their connections are now described. In this figure it is assumed all software for both sensing and display is located in the same PC 25. In some cases shown in FIG. 2, there may be a separate connection to a game console (such as Xbox) where game graphics and audio are processed in which case the PC (or other suitable computer) is generally used for just the optical sensing and other input processing. With suitable access to the computer software of the game console it is possible to have all inputs processed in the console itself, as the disclosed method of processing is simple and does not consume much compute power of the game console (or PC, or any other suitable computer).

Inputs include data from one or more cameras used to sense positions of points on the rider, bike or objects, or to obtain video to transmit to others (or record for future use in analyzing performance for example,) microphones to pick up voice commands if used in the activity, and instrumentation such as Heart rate monitors such as those by Polar Corp or equivalent used, interfaced to PC 25 of device and able to provide all data on the display as desired. A transmitter belt can be used around the chest to transmit the data directly to the pc device. This allows the maximum knowledge to be able to be imparted to the bike rider for serious training and exercise. Monitor of heart rate can also be used to flag potential unsafe conditions and warn the rider by audio or visual displayed data on display 24 or both. Comparisons of heart rate parameters to previous data can be provided on the display 24.

Outputs include besides the display and audio speakers, for both computer prompts, and voice from internet connected persons and the like. Other outputs could include vibrators such as piezoelectric types to vibrate one or more portions of the exercise machine, such as the handle bars or seat in response for example to game activity (like driving on a washboard road). Such things require specially equipped exercise machines and wiring, which otherwise is not generally needed unless LED type targets are for example used.

As the person 1 pedals the bike and undertakes both the exercise and the fun movements of any game associated with the bike, the various camera monitored points move in space, and the positions of the points at various time intervals are obtained by camera 30. These image points are processed by the computer 25 (including software either specially written, or standard machine vision software such as the Matrox Corporation MIL image library Information is obtained that monitors the position or movement of the person or bike features or other objects used. This information can be used for teaching or diagnostics or to more generally to drive the display and voice related portions of a game program. These programs are resident on a game controller or pc, and might optionally be downloaded from the Internet or used to interact with other persons on the Internet.

The first game to be described herein is a bike tour through for example, the streets of Paris. The speed of the bike and rider in the displayed image is in this case a function of the speed of the real exercise bike 5 being pedaled. To turn left, the rider leans left in this example, and to turn right, leans right. The change in target position of a feature on the person such as their head, or neck or other portion is sensed, and the rider displayed on the screen turns accordingly. Such sensing is aided greatly in both speed and resolution in normal room conditions by the use of the retro reflective target datum's described. Alternative to sensing the person lean to effect a turn, one can sense a hand movement such as the conventional right or left hand movement, or some other movement of the person can be sensed. Or as pointed out, we can equip the bike at extra cost with movable handle bars which can be sensed. We can also sense a three or four point target set on the person's headband or hat and easily obtain a movement of the head, as well as the viewing direction. This could alternatively be used for the turning function, or in a more sophisticated program, to actually act as the persons view point—who might look to the side for example, to see some danger approaching. This is particularly effective with large screens which give an immersive effect, especially if they tend to at least partially wrap around the sides of the person, an extra cost feature and normally not available in ones home. This can allow bad guys to approach more from the sides where you might have to turn and shoot for example.

Shown in dotted lines in FIG. 1a are optionally movable handlebars 6 (dotted lines) employed for giving the bike a steering function re a game displayed on the screen. This movement could be locked for playing other games such as strenuous spinning ones, where movement might not be desired. As shown, the rotational position of the handlebars can be determined with a single camera 30 through trigonometry related to the angle alpha of the camera axis (see FIG. 1b). As the left and right handle tips 58 and 59 of the handlebars move in unison one toward the other away from the camera as the case may be, the position of the points in the field of view changes accordingly for example. Resolution of handlebar movement improves when a substantial angle alpha (eg>20 degrees, and often more) is used.

The actual graphics displayed can be generated using 3D graphical means, and represent virtual situations like today's video games. But they can also be comprised of real footage of scenes as described in my copending applications and patents. These can be used to provide a succession of video clips, whose play on the display is a function of the actions of the player. Touring through Paris is an example, where real shots of street scenes can be used. If you virtually bike up the Champs Elysee you see to the left and right the real image. This can even be made more exciting, by having a clip of a car sideswiping you, where you have to turn off the street to avoid the danger, and then go up another street. This makes travelogues much more interesting.

It is alternatively or additionally possible to locate the camera and light source (where needed) in the rear such as 50 shown in dotted lines in FIG. 1a. This arrangement has an advantage that the light source is not pointing at the eyes of the player, allowing then visible light rather than IR to be used. This allows conventional low cost webcams as inputs and further allows color differentiation of colored retro reflectors, or other colored features of the person or bike. However, strong light along the camera axis from the rear (such as useful with retro reflectors) can hit the display and reflect back at the rider or washout the display. It can then be desirable to move the camera 50 off the display to bike axis 23, for example to position 'P'. Generally it can be arranged that most points on the person and bike needed for a game are visible from this position.

Note too that many shoes today such as Nike brand have retro reflective targets on the heel (for running or biking safety at night) which can be used here as well. But in general, with the rear mounted camera, there may be fewer points that can be seen, and it is sometimes difficult to find locations in the room to mount the camera and light source. Thus targets may also be desired on the toe or sides of the shoe, in addition or instead of on the heel. While the camera can be connected to the PC 25 via Bluetooth or other wireless means, battery power can be somewhat difficult for the LEDs as they use considerable power, unless one admits to recharging fairly often. Thus it may be desirable for wires to be used at least for the power, which may or may not be easily accomplished.

One may employ an alternative (or optional) side mounted camera also shown in dotted lines 51 in FIG. 1a. This generally doesn't both the rider unless very bright For some types of exercise this is a preferred location, for example if a particular type of walking or running is to be analyzed such as might be used in a treadmill related applications. In this example the shoes can have targets on the sides, for example to see the motions of the feet. This allows persons jogging on the treadmill to compare strides for example over the internet.

Using body signals (such as leaning one way or the other—sensed in this case by head motion going left or right), or using ones hands to signal or by providing steerable handlebars whose position can alternatively be sensed one can also provide a game where you are bicycling down a path that led us a simulates the Tour de France or some path through your town or other things that the such as mentioned in previous applications. If you are actually peddling the bike in these situations it can be a stationary bike. Or it can be a road bike that you put on rollers such that the wheels do not contact the ground. In any case, the motion of the wheels can be monitored as shown above as can the position of the handlebars including rotation thereof if permitted, which are now discussed in further detail.

Let's move now to the case of a group activity such as a spinning class, also called indoor cycling, studio cycling, or other names. Spinning exercise classes usually consist of about 12 to 20 people. Classes range from 50 to 60 minutes and are set to music. The instructor takes the class on an imaginary ride that includes all types of terrain that produces a great spinning workout. If one is a type of person who doesn't care for traditional exercise classes, this form of exercise can be useful. One of the many benefits of spinning is you feel like you're keeping up with the class because everyone finishes at the same time. A special spinning bicycle may have a weighted flywheel in the front and makes you feel more like you're riding on a real bicycle. The spinning bike allows you to adjust the tension to keep pedaling within a comfortable range for your fitness level.

A new feature now added by the invention herein is to allow this spinning activity to occur with a virtual instructor, and/or with a class of one or more other persons which further may be remotely located but linked by the internet or other means. In this particular example a person can ride their bike in front of the camera and the screen. However on the screen, we can also produce the image of a spinning master or instructor who would then give commands and suggestions to the person riding a bike. These commands and suggestions can come from a pre-stored program, but can be in direct response to the determined positions and motions of the person and they portions of the bike that are being monitored by the TV camera and computer. For example, the instructor might say, "let's sprint". A person would then lower their head and began peddling faster. The camera system can determine that they indeed are doing this and in addition to determine how fast their peddling from the movement of the pedals noted that for a given bike and pedal locations with respect to the diameter the wheel. The rate of motion can be determined, and if the resistance of the machine is known, the amount of energy being burned.

If the program determines that the person is not pedaling fast enough, an indication may be made either visually or vocally, such as the instructor might do that is to say pedal faster. Could also say the rate for example, you could say you are pedaling at 10 miles an hour try to get to 20. And so forth. The stored program could say raise hands, and then monitor how high you raise them. And if you did it at all. While just words can be used, one can also have a virtual instructor graphically making gestures, as well as moving his lips to say these things. All of this can be done using motion capture 3-D video and video clips of actual instructors can be called up from memory as needed and alternatively used This is especially workable if one keeps the various instructions to a limited dictionary of such things. When one is using digitally created voices as opposed to actual voices one can then put in the names of the person themselves to personalize more easily. It could say say Susie, you're going too slow.

And you can have a real live spinning instructor too, communicating over the net. He can see all his class on a composite screen with all their images and see their performance data coming from the camera systems if he so desires. This aids him in making suggestions to the class. While discussed here with spinning it could be ballet or other types of activity done this way.

In the above application relative to stationary bike use for spinning there is no particular need to monitor the handlebar locations at least on a typical fixed handlebar exercise bike. However one may add an auxiliary handlebar or modify the bike itself in order to create handlebar position related activities. Or one can use another bike having such handlebars. Target datum's if on the shoe (eg toe, heel sides) can easily be monitored with the camera of the invention to obtain rate of movement, if monitoring pedals or other targets providing such data like is not desired.

Besides monitoring wheel speed and steering/handlebar location, one may also use the camera to determine real (that is actually actuating the bike brake such that one has to expend exercise to accelerate it again) or simulated brake position that can be used in games to brake the bike. For example the person whose character you are in the game may need to stop its motion, either on a bike, in a plane or car, or walking. In this case you need to apply the brake, though it might be of time value to make it not be necessary to fully stop the real bike wheel in order to effectively cause a stop of the character's movement in the game. Other game related modifications may also be done by application of the bike's brake or other bike functions if any. The same holds true for application of the invention to treadmills, Nordic tracks and other exercise machines.

The camera based computer program resident in computer 25 can also be used to help determine that you should not go beyond a certain limit. This is especially important for rehabilitation and for seniors exercise. This can be a limit in terms of the extension of your arm or the number of times you extend your arm a certain distance for example. Or it can be limits that have to do with ones accumulated energy expenditure. Other exercise related variables can also be monitored. This can be particularly useful for those people who have had some sorts of problems that they are trying to rehabilitate, for example stroke victims. Older citizens can benefit too. It should be noted that the invention as well, if it determines some sort of an unusual activity going on or one that could be dangerous could also automatically query using techniques known in the art to Internet sources for medical advice. This source could come from the manufacturer of the machine or elsewhere, and can be not only medically related, but related to other issues such as those of the machine itself.

In some applications, one can monitor either points on the person alone or the person and points on the bike (or other exercise equipment), or on the bike alone, in order to obtain the desired information to control the game. In some bike examples it is possible to provide games which just use the points on the person, since all points on the bike which are moving are in turn person movement related. For example if you monitor movement of your knee or toe up and down, it gives the same cadence result as monitoring the pedal movement up and down on the bike. Movable controls mounted to the bike or other exercise equipment may also be advantageously monitored directly with the camera system (switches, levers, handlebar movements, rotating throttles on motorcycles, etc), and fixed points on the equipment may be used for a calibration.

FIG. 1c illustrates for example further types of target members of the invention which may be useful in the activities disclosed, such as bike race games and the like. For example collar target 280 useful for determining from the camera image if a persons lean left or right, and stand up or lean over in the bike, when viewed from camera 30. A targeted belt buckle is useful for stand up motions in this example. Another example are ankle band target 84 and 85, which in a bike game are useful only in certain circumstances where such movement can be correlated to a game command, though the angle like the toe could be used for determining rotation rate. Targets may be either bands, or cable like, made of retro reflective material such as scotch light 7615 or another scotch light glass bead type, generally cloth backed. Any or all may be used in a particular game or activity. In addition there are point, or point grouping, targets which may be used, such as the three or 4 point target sets which may be on head bands, hats, the back of a hand and the like. Suitable targets allow up to 6 axes of position and orientation of the object to which they are attached to be determined as disclosed in my referenced applications and patents. The retro reflector near IR (820 nm) signal to noise ratio of a typical target in a daylight bright room was measured at 300:1.

A target may be part of apparel such as shoes having retro reflective material on the toe and heel regions. Targets around body parts such as arms, fingers, neck, wrists, ankles etc can be bead type, with a rope like material covered with retro reflective tape, or can be plastic bands for example of larger width with retro reflective tape on them. Necklaces may also be of retro reflective material. In addition, targets utilized may be colored in order to code which target is which, if necessary, which works as long as a color camera or other color sensing electro optical sensor is used to determine their location in space. IR "color codes" can also be used, if different near ir sensitivity filters are used on the camera, like Bayer filters for visible color. Targets used may alternatively or in addition be coded by shape. For example target shape could be a diamond, or for another example a circle of retro reflective material 87 on the toe of shoe 88 having a non-retroreflective black appearing line 89 within it. It should be noted that targets can be irregular and seen as blobs by the camera, and tracked in much the same way. Non-retro reflective portions can actually carry information such as the clothing or shoe manufacturers name or logo.

It generally is not required to code the targets to identify them if exercise is conducted on a machine or in other position controlled situation with limited ranges of human movement in the game or activity. However, it should be noted that coded targets help to discriminate against glints from shiny objects such as door knobs and chrome chair portions which can cause confusing reflections that can look light bright retro reflective targets. If all targets were circles for example like 960, it is unlikely anything else would look like them, and thus this shape can be used as a differentiator. Subtraction of background signals can be used too as discussed below. While more expensive, 3D camera can also be used such as that of Canesta Company, and in this case objects in the background can be discriminated out by range.

As noted elsewhere herein and in previous work, bright contrasting colored targets can be used, without benefit of retro reflection as long as sufficient light is available. The beauty of the retro material is that in relatively low room light best for viewing the display, the retro material gives strong signal to noise without being obtrusive. And the Led's and camera use little power, thus potentially allowing them to be battery powered and wirelessly communicate camera and led control information to and from the pc or other computer.

As I've pointed out in the referenced co-pending applications, the target points can be natural features of the object itself, which are recognized by processing the image data. Or they may be specialized points, which can either be part of the object for example light colored dots (or other portions) on a headband or can be attached to the object for example a plastic retro reflector. Retro reflective tape or cloth material can be sold or attached to objects very easily and is has the advantage that it is flexible. However plastic corner cube retro reflectors and cat's eye types can also be used. As I've pointed out previously such retro reflective targets are very useful in that they have of very high contrast with respect to their surroundings when illuminated by light that is more or less on axis with the camera as the particular light shown is as the LED or LEDs mounted next to the camera. Note that flash sources as well as continuous sources can be used, and including ones synchronized with the camera shutter for maximum background noise rejection.

The preferred feature of a person or exercise object to identify and track with a camera (or other electro-optical sensor) in conjunction with such activity is a retro reflector or a light emitting diode in some cases, and if power is not an issue. Retro reflectors provide very high contrast with illumination on or near the axis of the camera, generally enough to distinguish them from any other sources of light in a room on brightness basis alone. However, there are situations such as glints from door knobs and the like, where one might have a potential problem. This would be particularly true it in a freestanding situation such as FIG. 4 or 5 where you were trying to illuminate a large area that someone was doing exercises or dances or other things in. In this latter application, it is also possible to use targets can be distinguished by other features than just contrast. For example by their color or by their shape or both as has been pointed out in previous applications and above.

The rope or band type arm, leg, head, wrist, or ring type targets all have a general shape which can be recognized as apart from other things such as typical glints, or white diffuse items for example. Their image appears considerable longer in one dimension than in the width dimension. And to further code them, one can easily make them have black bars running across their width for example.

It is also possible as previously pointed out to simply use color or shape or both as a means of sufficiently recognizing the targets with respect to a background. In this case, no special light IR sources are utilized and no special on or nearly on the camera axis lighting is necessarily required. The targets appear in the image taken by the Webcam 34 (and may be used with the webcam 34 instead of camera 30 for example), but this appearance of bright spots in the image (particularly with retro reflectors, if used) may be perfectly acceptable in some cases. The drawback of using such features that are not high contrast reflectance is that typically one may have to run a particular computer based system slower in order to process the image more in order to recognize the targets in the total image field. In addition, there may be more danger of confusing the target with some other feature such as a something a person would wear.

The case of an exercise bike such as noted here though is one where things are relatively constrained in this regard as the room with the bike and clothing are under control of the user generally speaking. So that a bright yellow target for example is generally discernible relative to the bike and typically the targets are generally within known regions with respect to the bike and can be looked for by the processing system of the computer in those image areas to correspond for games that are set up to recognize signals made by the person in certain regions of space. This is an important simplification, lowering the cost of the camera computer portion, and increasing reliability of use.

Even more generally, there are certain situations here where you might not need any particular targets at all. In other words, you could use natural features of the bike or person. If you raise your hand up for example this may be quite discernible relative to the background of the room. If you move your head down or up, the same may hold true. Or you might simply use at a hat that had a different color which can be searched for by the image processing program, to help in rapidly identifying your head. Thus it in summation, the situation and the game itself may determine just how much specialized target application is required. And in some cases most or all of the targets one might employ may not be needed. In the same vein, it may be that one or more highly visible and contrasting retro reflectors are required if fast motions of certain points under any circumstance are to be encountered. It is also clear that as processing speeds continue to increase in the inexpensive PCs or game controllers one might use, then less and less specialized target information may be required in the future to operate the "exergaming" system of the invention at the speeds and accuracy required for good motivation and enjoyment.

Generally speaking though, a goal of the invention is to provide reliable performance at the speeds needed, from low cost equipment. The retro reflector approach does this without wires or batteries as LEDs require (which also can give good signals, and give color coded ones, without worry as to bright light in the persons eyes. While retro reflectors provide high contrast when using coaxial incident illumination, self-luminous targets such as LEDs can be used, which have high contrast in many cases too? LEDs can be battery powered say by a battery pack on the person and/or the machine. In this case they can operate if desired in the visible range as there is no need for light in front of the user's eyes. The LEDS can be colored too, to allow their separation one from the others. And they can be pulsed at a frequency, which can be synchronized with camera shutter to maximize signal to noise.

One can relatively easily also add highly visible features such as retro reflective targets or leds to accessories used by players of these games such as retro reflectors on IPOD ear phones for example, to be used to determine head pointing direction or head height. Objects held by the players can also be targeted. It is for example possible to target a conventional game controller pad with a 3 or four point target set and determine its position and orientation in a game, perhaps used for flying a plane for example. Moving a game controller by small orientations and positions, would defeat the exercise benefit of the invention however, just as it can for the Wii example mentioned in the introduction.

One or more fixed portions of the bike (or other equipment) can be provided with fixed targets such as with target 53 and 54 shown in FIG. 1a on the bike frame. Such fixed targets can be used for set up, calibration or reference purposes for example. And these targets when used with targets for example on the handle bar ends 59 and 58 when handle bar is fixed, or the bike is in the straight ahead position, to give a full 6 degree of calibration of the camera to the bike, as 4 points of known spacing (e.g. the distance D) in a pattern which can be used with the stereo photogrammetry method of Pinckney et al and others. This means the bike or camera may be moved and the whole system recalibrated in the computer such that positions on the bike or of persons on the bike can be known with reasonable accuracy with respect to the image on the camera matrix array which is digitized and used to determine these positions, and any changes therein which are desired, then in real time. If the handlebars are adjusted up or down, this amount can be changed by entering the amount moved or using the camera once calibrated to the initial setting to measure the value of the new handlebar position.

Figure 1D:
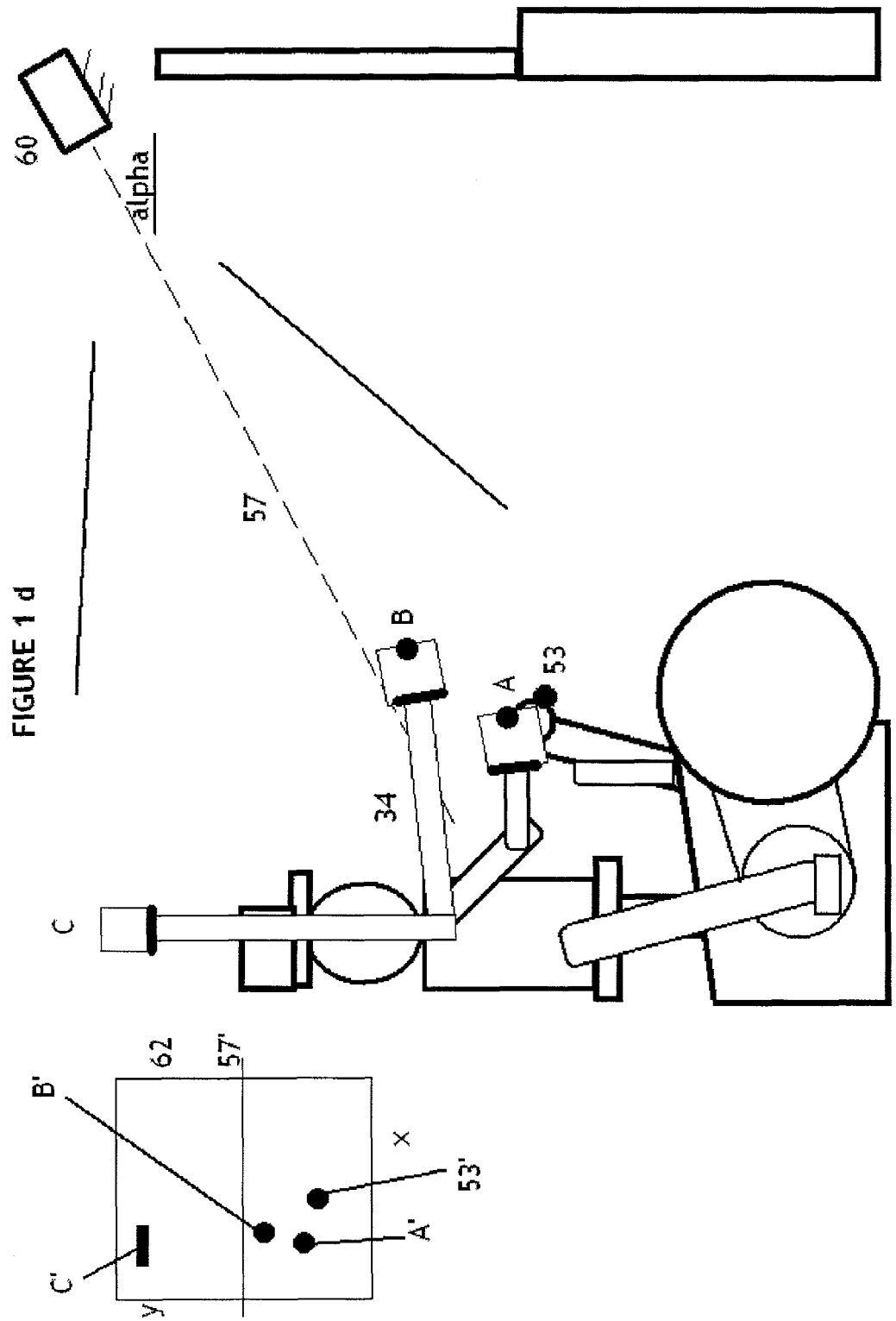
FIG. 1d illustrates calibration also as a function of a game.

FIG. 1d illustrates an alternative arbitrarily located camera 60 in the vertical (and/or horizontal for that matter) direction, which is calibrated to suit either the geometry of the set up, or the game function or both. This can be used in other exercise machines too like treadmills, Nordic tracks, Stairmasters, rowing machines, and the like. In this example the camera 60 is shown at an arbitrary location at an approximately 35 degree angle to the horizontal which also allows us to determine certain motions such as a punching motion of the players arm 34, typically in a direction more or less parallel to the bike axis and perpendicular to the display. The inset 62 shows the image on the matrix array of the camera from a wrist target in three different positions and at different times. Right hand high overhead C', punching forward B', and on the bike handle bar A'. If these are the only three positions the right hand can be in for valid activity, in the particular game, then it is only necessary to see if the target is in one of those positions. The measurement can be with respect to the camera optical axis 57 or to a local reference on the machine or other fixed object such as datum 53.

Bike and treadmill based games are generally good choices for exercise, as they leave the hands relatively free at least some of the time, such that one can use ones hands for various game commands. And ones head and upper body to a degree are generally available too.

If the person does not do a suitably extended arm punch, the image B' target point B will lie closer to the optical axis and therefore the centerline of the camera array. And by the same token it will lie farther from the image 53' of the fixed point 53, alternatively it can be compared to its original point A at rest on the handlebar, or wherever the person was resting. Limits can be placed on just how distant from the reference point chosen one has to be before registering a signal such as a hit on a virtual bad guy on the screen or whatever. Similarly limits on other positions such as the hands raised position C for both left and right arms can also be set. The soft ware can operate by actually measuring the amount, or setting up an ROI where nothing happens unless the feature in question enters the ROI and in this case it trips a switch that that function has been done, in much the same as a game pad switch might do the same function in the game. As opposed to tripping a switch, one can also activate the switch which keeps the function on as long as you are in that ROI location. For example, if one uses the left arm straight out position to indicate the wheels of a virtual car on the screen should be turned left, then as long as your left arm was in the ROI for that function, it would cause the car to keep turning left.

Another point is that you can have a special target, in which you have a round target 64 on a mitten such as 65 which faces forward and is entirely different shape than the wrist band target (which itself could be on the bottom of the mitten, in one style). Then you look for this shape target (and generally a bright indication there from as well) to indicate punching actions. Moving from a position on the handlebar to a position out in front.

The use of a single camera with a simple 2D image plane to effectively obtain 3D data of this kind is made possible in consideration of a specialized set of game positions possible, or through the use of target sets or types whose baseline allows one to acquire a degree of multi-axis information from one camera using stereo photogrammetry. In other words to effect a game of the type described herein on an exercise machine, it is generally not necessary to see a whole range of possible 3D movements anywhere in space in front of a camera, but rather just those regions where certain types of movements or positions are likely to occur as required by game play. This is an important simplification.

It should be noted that a camera mounted off to the side can also achieve similar results, such as camera and LED sources 37 mounted at angle gamma in FIG. 1a with respect to the axis of the bike.

In relatively few occurrences or regions sophisticated orientation knowledge is needed. The ones most often of interest are first the orientation of the head (as opposed to just xy head position) which orientation for example may indicate a gazing direction of the person and can be used to change the viewpoint of the displayed image. Also useful in many games is the orientation of a object such as a pistol or your forefinger which one might point at something on the screen. In this case one can observe the shape for example of a cylindrical target on ones fore finger or the gun barrel in order to approximately discern pointing direction for example. This has been discussed in my aforementioned cases incorporated by reference. When pointing with your forefinger as a gun barrel, you can move your middle finger and cause a trigger signal to be detected by the camera, for example using movement of a ring shaped target retroreflector on the end of your middle finger.

Let us now illustrate more or less classical video game forms (available on Playstation by Sony and XBOX by Microsoft) which can be played using the invention while exercising on a machine and thus motivating exercise at very low cost compared to the cost of creating special exercise software as might be desired for maximum benefit. It should be noted that one can even use the camera and computer system of the invention to play video games while not exercising, if so desired. This allows people who are confined to wheel chairs for example to play, using movements of their heads, hands, neck or whatever can be targeted reasonably and seen by the camera.

The invention also makes possible classical video games when the person is not on a machine but rather in free space being observed by one or more cameras.

It is also noted that the person riding a bike (or otherwise engaging in activity as disclosed herein), may as part of the activity holds some object such as a pistol or wand or other game related thing (or exercise related such as a weight, which also may be used in a game) in their hand, which they could raise up or move in some direction at would be interesting for the a particular game. In this case the object can have highly discernible targets, and perhaps it is not necessary to target the persons hand, finger or wrist though this depends on the game in question. Things that would normally be used in the process of the activities would be the machine itself, an object a player would hold, and/or perhaps a piece of clothing for example. Other objects can for example, be sporting equipment such as baseball mitts, tennis racquets, balls, hockey or lacrosse sticks, cricket bats, on so on. Or it should be noted, they could be play objects attached to the machine for gaming purposes. One example would be a plastic car steering wheel which could be attached to the fixed handlebars of a spinning bike (or the frame of a treadmill as another example) and the steering wheel monitored for its angular position by the camera.

Lets also consider that the person is playing a video game of the classic first person shooter type which is running on an Xbox360 game console, where the exercise bike riders avatar is displayed in the video game image (typically at the bottom of the display).The goal is to move this avatar (which may in the original video game, be a car) thru various streets or whatever, shooting bad guys along the way, and in some game specific manner amass the most points. The Xbox controls a display, and takes inputs from a PC which processes signals from a camera. The associated LEDs for retroreflective target illumination if used, are not shown for clarity.

In a drawing similar to that of FIG. 1d, consider that the player is not wearing the targeted mittens of that figure, but rather holding a pistol in his right hand and having a wrist band target on his left wrist. While in this case the person's finger or hand may serve as a gun, using say a cylindrical (or other multipoint) target as mentioned above on a finger, to obtain effective 3D pointing direction, in this example, the person on the bike holds a model pistol with a cylindrical target on its barrel, which can be easily identified as such (since the pistol may be waved around and pointed at different locations on the screen where enemies appear, as one example). This setup also makes use of a LED emitter target at a wavelength able to be discerned by the camera, said emitter, with its battery to power it, located on the hat of the player.

In this game the hands raised position has for example, not been required, and the lens (or camera chip, if digitally restricted) field of view is shown limited to a narrower angle than in the game situation of FIG. 1d. This can provide improved resolution or speed for example.

Other game functions can also be sensed as well by the camera, for example the position of an attachable play device such as throttle lever 21 mounted to the handle bar in FIG. 1a, or the position of, brake lever 13 as another example. A trigger actuated battery or magneto in the pistol causes an IR LED inside the end of the barrel to momentarily emit light, at a wavelength visible to the camera and thus able to be sensed by it when the trigger is pulled. The light then appears in the image array 62 as such shown as shown in FIG. 1d. Other things in this system are the same as in FIG. 1d. Just this function, the pistol, plus the ability to track head position and orientation plus rotation rate, can make an exciting game.

Note that some variables, for example rotation rate, could be provided by conventional means if desired, for example a shaft encoder in the rate case. This costs more, also to interface to the PC 25, but it would allow the camera FOV to be reduced, if no other variable near the bottom of the drawing (e.g. toe kicks) were being observed in the game.

The target that the pistol is pointing at alternatively may be sensed by other means. For example a camera to observe a laser beam coming from the pistol and where it hits the screen, and thus the displayed object at that position on the screen. This camera would be interfaced to PC 25 which would then coordinate the information obtained with knowledge of the display graphics being provided to the display.

Attachable play control devices such as levers, switch buttons, sliders, knobs and the like, which may or may not have any actual exercise function, can serve as an alternative or additional input to the game in respect to looking at a part of the person's body such as a hand signal, or to listen via microphone 28 and voice recognition software for a verbal signal (such as bang, for a trigger function) to indicate the presence or value of a variable in the game.

A person biking in the above example or a participant in any game of the invention herein, can be sensed pointing at something on the screen, and this can be used in game play too. For example, a Harry Potter scene in which his wand is pointed at a displayed person and a magical spell put on them, perhaps by also saying the word "shazam", or something suitable. The wand can have a cylindrical target or other artificial features to aid its pointing direction too, like the pistol In an alternative game type, described here for illustration of the many possibilities of the invention, one can provide a game where the bike is generally not steered as part of the game (though it could be). This is typical of what is called a rail shooter game. However, In this case the game may if desired be played a bit differently. The bad guys appear on the screen and appear to shoot directly at the bike rider in the room (rather than an avatar of same). The bike rider then shoots backs—physically at them, much like in a real shooting gallery or shooting skeet for example. This assumes the presence of a large HDTV display, preferably able to display the enemies' full size for maximum realism. This can be achieved with projection devices today. And the latest types of large plasma displays such as the 150 inch diagonal one displayed at CES in January 2008. The bad guys fall by the way side as the bike is pedaled thru various hazards (the bike for example, could be displayed as a Humvee Jeep type vehicle in Iraq in the video game display)

Another input might be to sense if you stand up in the bike, this triggers a signal for the Humvee to leap a chasm, for jump a building like Mario brothers tor example. If you lean forward in the bike, this is sensed, and if so programmed the humvee lower itself and go under a bridge, or alternatively this command could apply the brakes. Or alternatively this can be the case if you apply the bike brake, which is sensed as noted.

The same camera system of FIG. 1 and other embodiments herein can be employed for all kinds of different games and activities, and used in conjunction with many types of machines, or no machines at all, as will be further explored herein. It should be noted that several machines can be monitored if you have a few at home for example. Generally, if you keep the field of view (FOV) of the camera the same (by using the same focal length lens for example (you would simply move the machine you want to workout and play on to be within of the field of view of the camera. Or conversely, simply move the camera (and associated light sources if any)

to the machine. Or alternatively, have a camera and light source on each machine and connect that to the PC or game console, or whatever computer is running the machine vision program to convert the players positions and movements into game commands.

Classical Video games as just described are known to be very amusing to many, indeed in some cases addictive. This is reinforced by social play, with others on a network such as the internet, where things are not only competitive, but on a personal basis so. it is possible that the invention can prove a huge benefit in causing people to far more frequently use exercise equipment they otherwise would not use—and use it a lot.

The video game as played above can appeal to many persons, as there are so many games from which to choose. In an institutional setting for example, (such as a mental health facility, where patients are bored, and taking anti-psychotic drugs causing weight gain) the exercise machine or machines of the invention may be setup so that video games can only be played using the invention, and the exercise machine in its fundamental movement mode. If certain criteria aren't met (E.g. bike wheel rotation at X revs/minute or more, or treadmill speed over a number) the game won't work. This then causes the residents to want to do exercise, just to participate in the game. Even at low levels of activity this can make a huge difference. One can also make more sophisticated criteria too, such as 10 arm stretches a given distance per period as part of the game. In an opposite vein it is also possible to program the game to shut down, if limits of time on the machine or movement or rate are being exceeded for example, which could indicate an unhealthy condition that could lead to heart failure for example. These programmed settings can be chosen for the individual player as well, who can log in with their password for example, or some other means.

The discussion above indicates you can play video games of the classical type using the invention, using portions of your body or features of a machine or its motion which are sensed by a camera or other electro optical sensor. FIG. 2 illustrates a method of utilizing this information to run commercial video games running on game consoles (eg Xbox) or PCs. Many such games are controlled by use of a classical simple gamepad controller such as a Logitech precision game pad selling for about 10 dollars, but are here controlled by the invention to provide a new dimension of exercise based gaming which aids weight loss, muscle tone and general physical and mental health, while also providing the opportunity to diagnose illnesses.

Illustrated is a means to play an existing video game by using software to convert signals to those required to simulate the electronic response of the game pad (also called a game controller) used with the game console (Xbox, play station, etc) or PC. In this case we substitute optically sensed human and machine inputs for the existing game pad inputs. The aforementioned Logitech precision game pad has 4 trigger switches, 4 thumb switches and a D pad, which is a specialized "D-Pad" 4 way switch (see U.S. Pat. No. 4,687,200) Not all functions are necessarily used in any one game. Some more sophisticated game pads have one or more of these controls able to operate in an analog fashion, for example changing resistance like a potentiometer in proportion to the distance you push them in for example. This same function can be related in the invention to how high you move your hand for example, or how far to the left, or how much in angle you cock your head in any particular direction, or any other suitable parameter which may be sensed. It is also noted that some game pads have force feedback in the form of vibration of the device. This can at some complexity be added to the exercise bike too, in order to shake the steering, or vibrate the seat for example. And audio feedback can be used via speakers.

An emulator "black box" 200 can be used as shown in FIG. 2a where access is not available to the game code directly from the PC 210 (or other processor) processing the information from one or more cameras 220 used to process the point locations and movements of the person and/or machine as shown above. The emulator is programmed to correlate the inputs from the human and machine in a defined manner to the game inputs needed by the game program, which was originally written for conventional game pads or other such apparatus. This correlation (see for example table 2b) can be chosen by the user or others in whatever manner is desired to make the game interesting or useful for therapy, exercise, diagnostics or other purposes. In short, even though one might arguably lean to the left, to go left, it might be programmed in this case to have you move your left arm a given distance sideways, in order to exercise that arm for rehabilitation therapy purposes. For mental exercises, it might be you would choose some other action, like moving your right arm, or finger, or a lever. To illustrate this, an alternate set of movements to play the same video game pad analogy controls is also shown in FIG. 2b.

It should be noted that the choice of positions to trigger equivalent game pad controls in the game, can also be chosen in consideration of the ease and/or cost of image processing. And as the invention becomes accepted as part of game console play, the variety of motion signatures that can be used as inputs can be much higher than those one might equivalently do on today's game pads. For example, one can program a certain input to the game to have occurred if the player makes a "Z" gesture with his hand in space in front of him while riding the bike of FIG. 1. This requires higher tracking speeds and more sophistication in terms of potential confusion of data from other portions of the body or bike. These issues at the present time add cost and complexity.

Another such gesture is a throwing motion, or a racquet swinging type motion, common to sports games such as MADDEN NFL by Electronic Arts for example. A person on a bike can make a football throwing motion, which for a realistic throwing experience can for example be determined from some starting and finishing point in space defined by the wrist of the player in making the throwing motion. This is better and more natural than possible with a game pad today. The resolution and tracking is helped because the bike has fixed the player more or less in a given region of space. This is actually a big advantage of the invention in that I have been able to localize the processing requirements allowing simple reliable equipment and ease of setup.

With more advanced image processing than normally required to make game pad type inputs using ones exercise, the ability to track sophisticated movement with the camera allows us to place values on the "quality" of movement, relating to path traveled and the timing of movement at points in the path. One can modify the game in fact to reflect this, with the quality of pictures and sound, or some other variable output depending on quality of movement and/or location reached—the simplest case being a big rapid stretch where you bike to attain maximum speed. A complicated sports movement would be another example. For example taking a tennis swing while biking. Good swing, gets score, or hit in the game. Or a bigger score, or some other choice of reward. All aspects of the exercise can be scored as the basic data is being taken. If desired, heart rate can also be monitored and added to a mix of score determinants A very interesting feature of the invention which is subtly illustrated in FIG. 2*b*, is that the same game, lets say a game that a person really likes and regularly plays with friends, can be changed in its command structure to provide a different form or level or other aspect of exercise. This can be on the same bike, using different hand motions one day, and going fast the next with hands on the wheel actuating handlebar mounted levers. And then the game can be played again, but set up on a completely different machine such as a treadmill—an exercise machine often found in the same location as a bike. The self calibrating aspect of the invention makes this easy to move, or one can just have cameras and light sources at each position, and switch over the computer and/or game console used. And even more static forms of exercise activity can also be used as game inputting devices, such as elliptical machines, bowflexes, etc.

The player of games such as those above, could using the invention be someone in a wheel chair for example, who can control the game as disclosed above for example by using their upper body motion (e.g. by seeing a neck collar target such as 280 in FIG. 1*c* or head band or hat target or their arms (which could have an upper arm band target such as 539 in FIG. 5) or targets on their hands or fingers.

It is noted that on a bike or treadmill for examples, the rate of motion is proportional to the exercise and in general, the calorie burn undergone. The game itself can encourage higher rates at certain points in the game for example, the bad guys car might speed up, or they might run faster or whatever. To keep up, you would have to pedal harder. If you shifted to a lower resistance (Eg using the resistance knob of the bike as disclosed) in order to do this, you might say lose points, or have less bullets to fire at them or some other game variable would be changed in relation to you changing an exercise variable.

This also holds true in social games such as spinning where you are playing or otherwise engaging with other members of a class.

One can while biking or tread milling (or in general) use a free hand to operate a hand puppet like FIG. 5 of referenced application 20060033713. This in turn can allow me to control a character in a virtual world such as in a game. The moves I make in a natural way learned in childhood for many, may be reflected in the character on the display which could be my avatar or a game character of some kind. The rate movement of the bike for example could be proportional to the rate of movement of this character in the forward direction. The 3D rigid body position of the hand puppet can be sensed as well has its head and hand positions with respect thereto as shown in the reference.

It should be noted that the game aspect of the invention can be further related to exercise goals by only allowing you to enter a command, if the movement required is correct. Or in another example, allowing it to be entered, but giving it less of a value or weight in the game, a point that encourages you to do more movement the next time. For example (of many possible) a shot fired by the pistol could fall short of its target, if the bike was not being pedaled fast enough.

It is now of interest to consider natural moves one can make while exercising on machines that might fit the classical video games created heretofore for use with conventional switch and potentiometer type game controllers. We have already illustrated biking faster to make a car, plane, or other object on the screen go faster. And applying the brake on the bike, to make it go slower (and the bike too, but maybe in a controlled and less abrupt manner). Another move is clearly to fire a weapon at some graphical image on the screen, while riding ones bike or on ones treadmill. This is another natural move.

More natural moves are hand signals learned for car driving to turn a virtual car on the screen, or to lean right or left to make any moving image on the screen go in that direction.

Moving ones head side to side or up and down is a natural way to turn, or rise or fall an image graphically displayed on the screen. This can be used to race cars, leap buildings, and so forth, and can be done by persons who are confined to chairs or beds.

Turning ones head to look one way or the other to cause a view point change of the display on the screen is natural too. Pointing ones feet in a direction of turn or up and down like the head motion is possible as well, as it is for the hands. Both can be easily tracked in 6 axes for this purpose with 3 or 4 point target datum sets thereon. The arm can be used for this purpose too, also with a target set on the hand, or a wrist band target.

Leaning ones whole upper body right or left may be used to cause in a game a car on the screen to turn, and one can twist ones upper body to affect this as well. Indeed with a 3 or 4 point target set on ones chest, one can make, with some difficulty, all 6 degrees of freedom of motion commands with ones upper torso.

Set up of the system can be accomplished a number of ways, all made easier when an exercise machine is used as a base for the gaming and exercise activity since it fixes the location of the person within some limits, and provides fixed points of reference for those limits within the camera field.

A first example of a setup procedure is now described relative to the bicycle exercise and associated gaming activity of FIG. 1. In Step 1, the camera and light source are positioned at an approximate distance from the bike, measured with a meter stick or other means, and aimed approximately at the mid point of the expected target locations.

In step 2, the computer such as 25 reads the camera image of reference points (such as 53, 54, 58 and 59 whose dimensional pattern on the bike is known a priori and stored in the computer) and calculates the position and orientation of the bike to the camera using single camera photogrammetry such as described by Pinckney. At this point, the computer knows where to look in the camera image for the other bike point such as the wheel target 15 let us say from a previous step. If not the computer using the loud speaker tells the user to put hold a target first on the wheel, and after storing that image, tells in sequence the user to try each other one, until all are known in relation to the fixed points on the bike. This step does not have to be repeated as now all points on the bike are known In step 3, the rider sits on the bike and the computer in sequence asks him/her to make the motions required for the game in question, or if a general setup, to go thru all motions needed for the game library, so nothing needs to be re setup. The person then on prompting may raise his left hand up high over his head, does so as a natural motion. The camera and computer registers this location, and sets up a reasonable ROI such as 44 in FIG. 1*c* around the zone where the wrist target looked at by the camera is expected.

Upon completion, it then prompts the person to make the next move. The prompt can be vocal, or it can be shown on the display, also graphically showing the user what to do using an animation. Prompts until all moves needed to operate the game have been so registered in computer 25. At this point the game is ready to run, and the limits of motion needed to trigger events can be set in if desired. For example, the user might say that only at the very maximum arm extension would it trigger a game action, or another user might say if his hand got within 5 inches of the max extension, he would like to trigger. The computer such as 25 can then use these limits in the game.

Similar instructions and prompts can be provided to explain to a person how to do an exercise, and to check or correct them if desired.

A modification to step one, can be to have someone just position the camera relative to the bike until the image of the reference points is on a certain location of the display on the screen of the camera image, corresponding again to the game in question. In other words the user would be prompted to move the camera in angle until the camera optical axis 57 in FIG. 1d more or less intersected the rider's chest. This setup procedure generally can work for any exercise machine, and is not limited to bikes.

If the camera has a zoom capability which is not really needed with most exercise machine examples, the zoom too can be calibrated in this way using the camera image to define how zoomed in the camera should be given the extension of the persons arms needed for example.

An abbreviated method of calibration is to just let the machine set the ROIs using norms for people, without requiring step 3. This is fairly accurate especially if one enters ones height or another pertinent variable (by computer keyboard, voice, or other means, even a hand gesture,). Unlike the step 3 procedure, this does not however account for user adjustments of bike parameters such as seat height or handlebar height which can otherwise be taken into account.

If by chance the person has moved into a position where the computer has set a ROI for a neighboring position, a prompt can tell this to the person—also visually on the display, and ask him to shift slightly in the movement he makes. Or the ROIs can be reset to not overlap in the computer. This assumes that simplified ROI based processing is used, and not something more sophisticated such as individual target identification and tracking.

It is noted that the invention comprehends designing a game such that the movements can be simple, for example to preclude overlap of ROI regions above when making the moves needed to make the game commands needed for the game in question. It is also noted that in time special games may be developed to take advantage of the capability of the invention to make inputs to games in new and exciting ways.

One can actually use ones own feel and experience with a particular exercise to calibrate some aspect of the machine or the game program. For example if you want to make a jump out of the bike seat a input to cause a machine gun to fire in the game, in order to perfect your jumping skills you can just change the program accordingly, overriding any preset program which might have the gun fired by a hand movement for example.

At this point I would like to more generally discuss the image processing and data gathering aspects of the invention. When clearly discernable targets are used, it is often not necessary for the camera to be well focused on them, though if small codes with in them are used, or targets are very close together, this becomes more important. For similar reasons, the optics can be plastic and low cost, and do not need color correction if an IR or other single effective wavelength source is used in conjunction with the camera.

The system as a rule of thumb needs to respond to approximately 20-30 times per second for each point, or in other words all the points have to be acquired and processed to determine their location in 1/30 second or so. This generally takes good signals visible well above the background noise level of the camera, both electronically and due to ambient light conditions in the room. For example, a bike being pedaled at 10 miles per hour, has a revolution rate for the driven wheel of 20 inch diameter 3 revs/sec approximately. To resolve this to 10 degrees requires nearly 100 readings/sec. But since the rotation data can be averaged to get speed over some longer time period, 30 readings per second or less will suffice. And most people don't go this fast either.

Another variable to monitor in some of the game motions described above is the rapid extension of ones hand in a direction. Many games need this data for a quick motion or action such as firing a gun at a bad guy. Here again if the readings are every 1/30 sec for the ROI in question, and the resolution is only plus or minus the resolution of knowing that a target has entered the ROI zone which could be either a switch function, or an analog function, that is where in the ROI is it, and with limits set up in the computer for defining the point at which action takes place. In this case one has to get a quick answer without a lot of data processing and this implies good signal to noise, as well as reasonable resolution of the camera such that the plus/minus one pixel error is not large. This latter is helped by looking at a relatively large target "blob". For example a target which is 10 mm in diameter for a field of view of 1 meter×1 meter occupies 1/100 the field in each direction. For a standard VGA camera with 640×480 pixels this is roughly 25 total pixels which can be used to register the event, not counting lens and blooming issues which may expand the number of pixels actually seeing light from this target.

A related target image enlarging issue however is blurring. This depends on the speed and the lighting method as well as the camera shutter method. Blur makes the target seem larger in the direction of motion, which may or may not hurt its resolution depending on what the game or motion is. Blur can be minimized and efficiency maximized by overdriving the led source with a higher current but for a momentary time after which the camera is read out in a synchronized manner. As long as the led duty cycle is kept within allowable current heat related limits the led will not be destroyed. Up to 10 times less blur and 10× improvement in signal to noise can be obtained this way, which is preferred to use if possible. Diode Lasers rather than Leds can also be used, safety aside, and can have very short high intensity pulses to effectively strobe motion and eliminate blur entirely.

There is also a potential problem with background illumination in the room. If an IR source is used, with a low cost band pass filter on the camera, then visible light from florescent or led lamps is virtually eliminated. However incandescent lights and sunlight can under certain circumstances cause background issues. Some of these problems, if present, can be eliminated by doing a background subtract at high speed, subtracting each frame from taken with the LED off from a previous frame with it on. This works well in many cases but reduces the number of points per second which can be obtained. It should be noted that a scanning laser camera employing for example a mirrorcle mirror brand mems scan mirror and a low cost red laser can be used, with a high speed photodiode detector and band pass filter. This has very high signal to noise, and may be desirable in brightly lit rooms or outdoors. However most exercise locations with displays that need to be viewed by the player by definition require somewhat subdued lighting.

Figure 3:
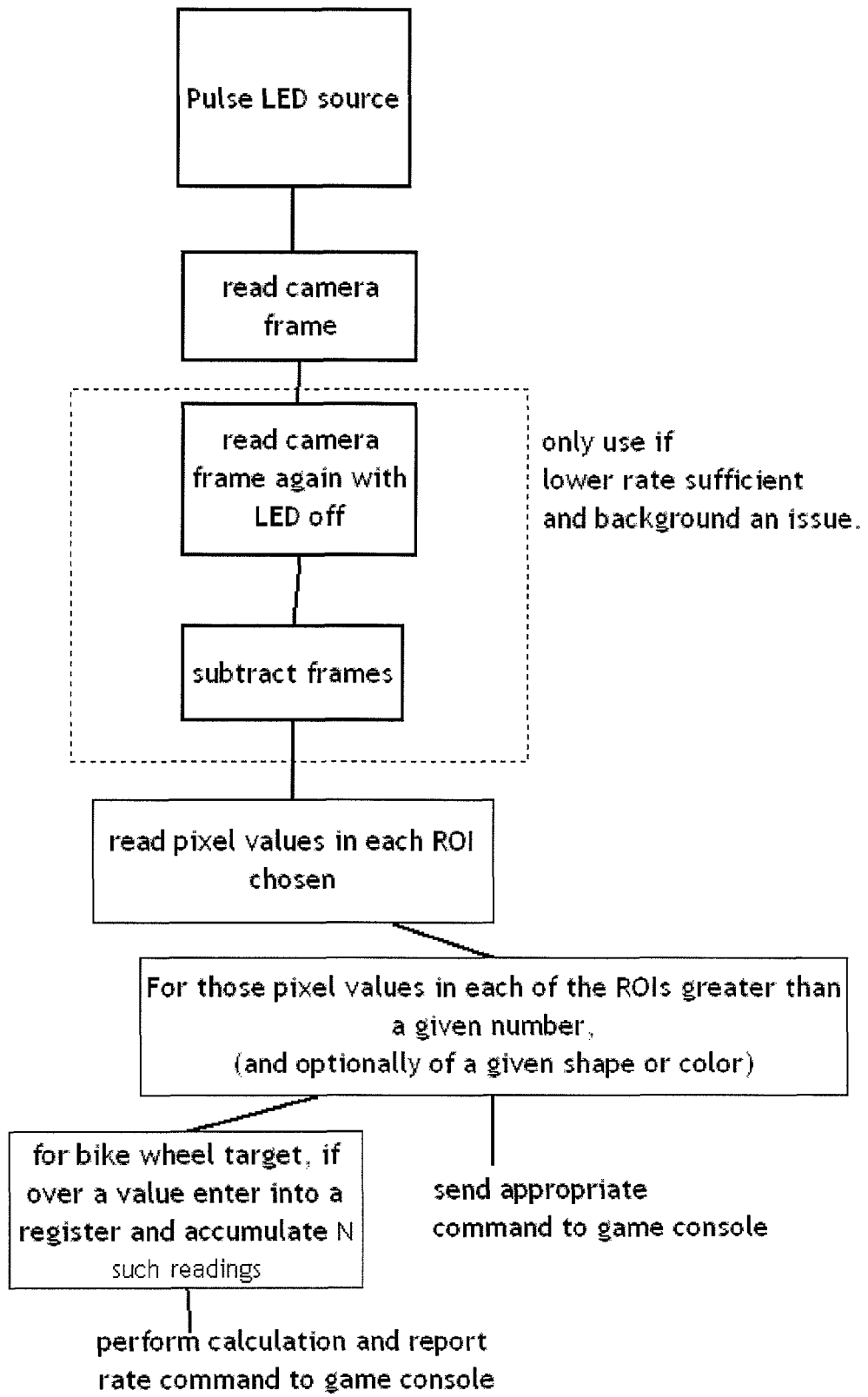
FIG. 3 is an abbreviated chart showing the flow of activity in one example of a camera based computer system of the invention

FIG. 3 is a chart showing one example of the flow of activity in the camera computer system.

For added information on use of single camera or two camera stereo techniques see for example, A paper by Dr. H. F. L. Pinkney entitled Theory and Development of an on line 30 Hz video photogrammetry system for real-time 3 dimensional control presented at the Symposium of Commission V Photogrammetry for Industry, Stockholm, August 1978, together with many of the references referred to therein gives many of the underlying equations of solution of photogrammetry particularly with a single camera. Another reference relating to use of two or more cameras, is Development of Stereo Vision for Industrial Inspection, Dr. S. F. El-Hakim, Proceedings of the Instrument Society of America (ISA) Symposium, Calgary Alta, Apr. 3-5 1989. This paper too has several references to the photogrammetry art).

A machine may be reconfigured to different exercises both mechanically in how the person may exercise against machine resistance, but also with respect to the sensing and computational software used to determine the location or movement of points on the person or the machine, and the display software which may be used to provide motivation and interest in the exercise. Bowflex by Nautilus corp. is one of many types of such machines that use cables pulleys and weights or tensioned members to exert force, but applied in different directions depending on the direction of movement of your hands or feet, and the setup of the machine.

The Bowflex or other reconfigurable machine has the ability to do many different sorts of exercises with one's arms and legs and can be configured in different manners. Your arms can go to the sides against resistance or in front or vertically. Reconfigurable machines are typically used in ones home in a bedroom or family room, similar to an exercise bike or a treadmill.

If you set up a certain resistance you can program that into the computer and in the easiest case simply say the words for the voice recognition program such as DragonDictate stored in the computer for example. "Resistance five". Then when you move your arms against that resistance to a certain extent, but the camera can measure it can Relates based also on the number of repetitions. The to do which it can compute the amount of energy you have expended and its any other. The invention also is helpful in displaying and/or verbally annunciating to you via a computer wav file called from memory for example that your motion was let's say not ideal in terms of angular orientation or position as you work the exercise is a helpful function of the invention in using such a machine. In a further embodiment of that idea, one can draw up on the screen for example; an idealized 3D graphic where your move should be and then you try to match your actual video acquired data of yourself in the movement to the graphical form. In a game, one might them "lose points" if they don't follow a correct path, or end up in the right location, or complete the exercise on time for example. And by monitoring extent of movement, repetitions, and directions and so on, one can calculate the energy expended in the session. One can even monitor to check the weight or other setting and automatically input that, similar to the barbell in FIG. 4b below As noted in previous disclosures, the invention can also be used for free standing activity of a person, without additional use of an exercise machine or other equipment. It is for example possible to use the same sensing equipment as long as the speeds of motion are within its capability, and the positions of features on the person can be effectively seen by the electro-optical sensor, or sensors, used.

Figure 4A:
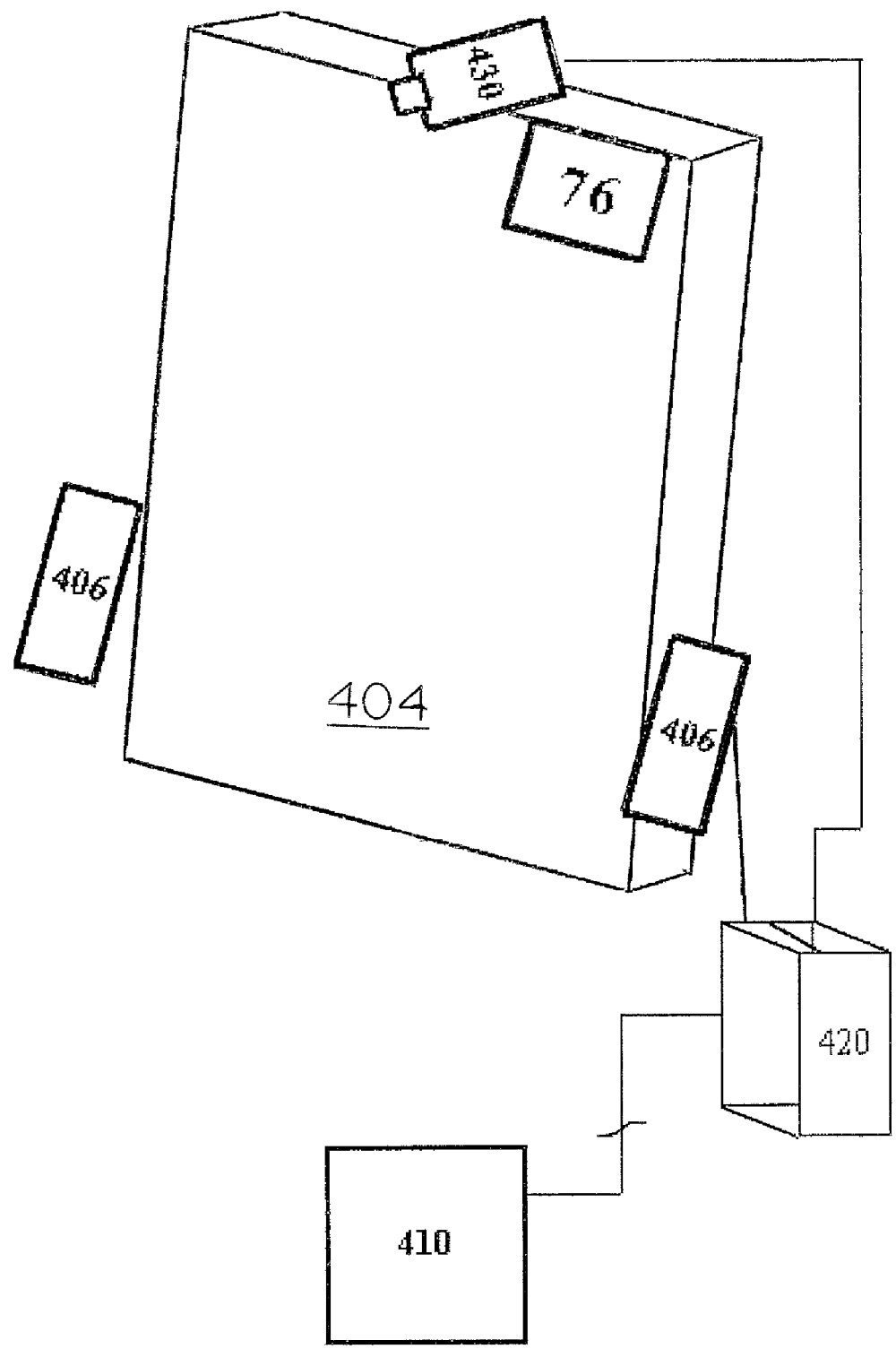
FIG. 4a illustrates an interactive workout video session

FIG. 4a illustrates an interactive session of a user of the invention relating to motivation for a given diet or exercise regimen, and employing automatic computer inputs of the invention, also providing dynamically changing data during exercise, which further allows one to see the effects on ones appearance of continuing a given regimen, or changing plans.

The system of the invention can provide either locally via storage media, or remotely via internet downloads, what is commonly known as a "Workout Video" to the user, but in this case tailored to the users dietary or exercise needs, and capable of receiving voice, position and movement inputs from the user . . . where such data is provided dynamically in real time, the workout video may be individually tailored, and even moment to moment paced for the user—just as if an instructor was present, who might say "you're not moving your arms enough", "go faster go higher", etc. If it goes too fast for comfort, the user can ask that the video slow down, and the video source respond accordingly so the users don't get discouraged. Rate, extent, speed of the video and music with it, choice of music with it and many other factors can all be called up on demand, and in response—automatically—to the users own actions.

Figure 4B:
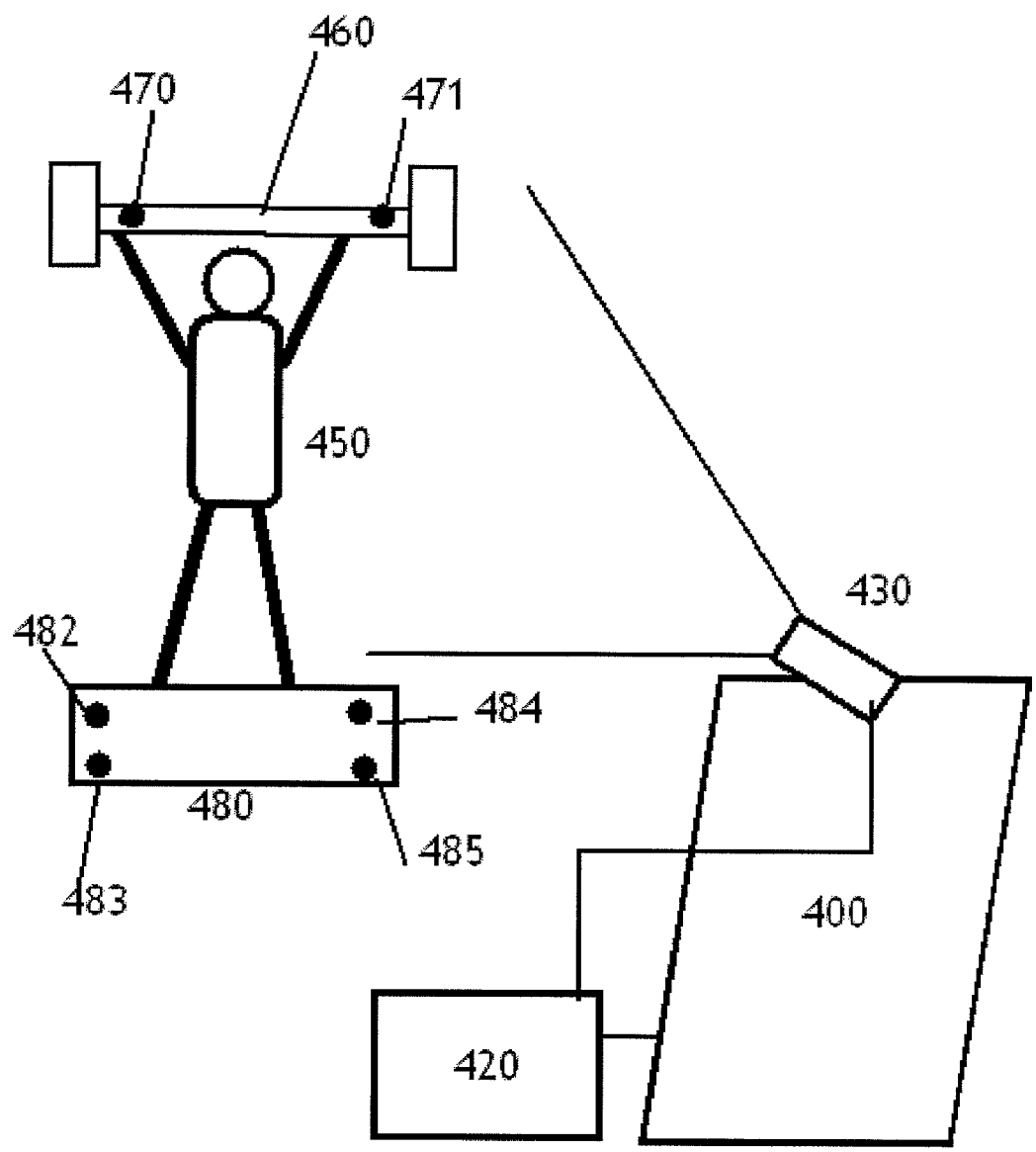
FIG. 4b illustrates a weight lifting exercise embodiment

A large screen display makes it more realistic, and speakers provide sounds which encourage activity—even computer generated sounds of encouragement like "way to go", or something taken as a direct input from the camera system which could identify that the users movements were good For example, consider in FIG. 4a a different scenario, in which a person such a person 450 in FIG. 4b and not shown here for clarity is doing a workout in front of display screen 404 which ideally is like a full length mirror, so to speak presenting images of others more or less life size. Input video digital images, such as that of an exercise instructor leading a workout are provided on screen 404 together with appropriate sound on speakers 406 from a remote source 410 connected by computer 420 via the internet. (Assuming a high enough speed data transfer link, to allow a remote source to be changed subject to inputs generated locally). For example as user such as 450 lifts his arms in the air, his hands are sensed in their peak height extension positions (for example) by TV camera 430 (and led light source, if used) connected to computer 420, which sensing can be aided by retro reflective wrist bands as described elsewhere herein. The positions in this case are just registered in X and Y, in the object plane of the camera, with no attempt to determine range, z, from the camera to the persons hands (possible with the "3D" stereo camera of previous inventions or the angled camera arrangement of FIG. 1d.

The arm extension and other x or y position values determined and the rate of change therein if desired, are reported from the computer 420 to the remote program source 410 (which could be resident alternatively in computer 420), which then can compare them to norms for that section of the work out video being presented—perhaps as well considering pre-entered data into the computer and thence to the program, of the person, such a age, weight, stature, starting condition, and medical issues if needed or monitored such as heart rate.

The program can then dynamically be changed, to go faster or slower, change programming entirely or whatever as a result of the input data and the dynamically changing data of the person, in this case his hand position and/or rate of change of position. And as mentioned, data can be fed back to the person as to how he is doing, both by voice generation in the computer, or by visual display on the screen, or both.

In addition, a score can be generated, just as if it was a video game. For example, a computed score for having the most motion, the most rapid moves, the most acceleration during the workout, etc. and this score can be compared to previous scores of the user, or to scores of others nearby or around the world using the same program for example. Such a score "76" is shown generated by computer 420 and provided on the upper right hand corner, in this case, of the display 404. Scoring can be based on an integral of moves, a mean, or any other tally desired. Some scores directly relate to energy expenditure and weight loss, while others could be just for "fun" so to speak.

In addition the data entered from your exercise can be used to actually play some sort of standard video game such as described above in FIG. 2 and elsewhere herein The invention thus includes a method of providing dynamically changing data during exercise, which allows one to see the effects on ones, appearance of continuing a given regimen, or changing plans. This data for example can be tabular data of projected measurements (such as weight or girth) or of projected variables such as heart rate. The data as noted in my previous or co pending applications can also be projected images of a person in the future. For example, if one set in a presumed workout of the same type for 30 minutes each day 3 times per week, the computer could provide a projected weight or other body dimension in 6 months time say. Or it could even show an animated model of you, shrinking in girth over time. Or with muscles bulging over time, or other related changes.

It is noted that a useful place to set up the invention is in a gym or fitness club, both to kill time, and to provide motivation for improvement. For example it is customary for many to watch TV while exercising on a treadmill for 20, 30 minutes or so. This time can be spent using the invention, which can present the images for example on a screen in front of the treadmill which can even be touched by the user if desired (using for example the touch screen technology shown in my co pending applications and previous patents), while walking. One can also sense the user with cameras, similar to what has been disclosed herein FIG. 4b illustrates another free form exercise embodiment of the invention, in this example comprised by weight lifting A weight lifter 450 in front of display 400 can for example, lift a barbell, 460, with camera 430 sensing his actions using computer processing not shown. The computer 420 provides via loudspeakers 406 inspirational sound and image for the weight lifter, and, as he lifts the barbell, the TV camera and image processing program resident in computer 420 can be used to identify the amount of weight lifted (by the number of weights on the barbell for example), and the height that it is lifted, and how often it is lifted. This data can be used to calculate the work performed, and other relevant training factors. And such data, plus a pre-entered knowledge of the person (and monitored information such as heart rate), can be used to predict the eventual outcome of the activity, or to predict the eventual size of various muscles etc. These muscles can be simulated on a digital model of the weight lifter as described above. If the activity is unsafe (too much weight, tilted bar, etc) the computer can sense this and advise accordingly as well. Too much weight after too long a time of exercise would be another such example.

The bar tilt can be calculated easily using retro reflectors 470 and 471 (as examples of target points)—alternatively the weights themselves can be identified as features to be used in the calculation) and the angle of the bar calculated from the positions of the retro reflectors in the image of camera 430. If the angle is deviating from horizontal by a amount of interest, a warning or other information can be provided such as providing an magnified tilt image of the barbell on display screen 400. It is noted that a bar bell or other freely held exercise object can be advantageously used, since the angle of tilt can be monitored to provide added safety and weight training data associated therewith. This is true as well for objects filled with liquid which can slosh around and add additional variables to the weight or other distribution of forces of exercise.

Clearly, the TV camera can be used for digitization of the activity of a large number of exercise activities for the benefit of the user. The display can include a digital model of a person or and the modification thereof, or could be any other kind of motivational presentation for example, such as a score, a comparison to previous data, a relative relationship to performance of a friend with whom one is having a social interaction session or whatever. The camera computer combination can be used for other beneficial activity as well, such as assuring that movements are not beyond preset or calculated limits or time integrals related to endurance and the like.

To illustrate the exemplary value of the invention for just one of the of the many potential rehabilitation exercises that need to be undertaken at us consider the potential use for improving on the invention of U.S. Pat. No. 4,199,137. This device is made for exercising an ankle in 2° of freedom of rotation vertically and horizontally plus or minus certain degrees from a straight ahead position. This relates to the problem of "teaching" of the ankle so to speak. The point here is that by suitable provision of a target datum viewable by the camera of the invention onto the toe for example of the foot of the person, a whole new experience can be provided to the person as well as movement data taken in multiple degrees of freedom for the use of their physician or therapist as to the exercise that they have undertaken in trying to bring their foot performance back to normal. In some cases the target datum isn't even needed as the movement is slow and the shoe movement may be seen at reasonable cost using the gray level image of natural shoe features. The display can be used to show the person under rehabilitation important data what to do, how far to go and how many repetitions they've made and can give them encouragement.

If the person is in the mood for a game it can for example be something where they do their rehabilitating repetitions in following a particular video character on the screen. It is also possible for the person in his home doing these foot exercises to communicate to another person having the same problem, who might be in another country for example. These people can find each other, be it via social networking sites, and can undertake little games such as those mentioned above, where one of the characters for example could be moved by person A and the other person B could use his foot to control a virtual gun to shoot it for example, all the while keeping the movements of their feet within the norms of the exercise. This is given as to be illustrative of the potential and not necessarily something that a doctor might recommend. But the point is that to make games around things that are possible and inspirational to people as well as to cause them to socially interact in so doing if they so desire.

It should also be noted that system can be programmed so the patient can see on the display when they are approaching a limit of their goals. While these limits can have hard stops as described in the aforementioned patent they can actually also be programmed in in software today for example a yellow were warning stop and then a hard stop for a buzzer with sound or a light was goal for something to tell the person that they've gone far enough. Probably more likely is that the person hasn't gone far enough because of the pain involved in teaching the foot once again, and in this case again the making some sort of reward system or interest level and going the full distance that is needed, but to the doctor's advice is desired to also noted that the data about what the patient is doing can be transmitted instantaneously over the Internet to a person in a rehab facility so the person does not have to be present. Indeed for example someone can be doing the exercise in question on the battlefield literally, where the doctor being in a VA hospital stateside. While this is been shown relative to the ankle movements described in the aforementioned patent.

The same sort of logic can be used for all sorts of rehabilitation exercises and because of the ability of the camera and optical system to measure its full 6° of freedom motions of the locations, and to measure more than one joint it is also possible to have relatively sophisticated types of rehabilitation as long as the person can follow the graphics and other information that might be generated on the screen.

It should also be noted that the patient can see when they are approaching the limit of their goals. While these limits can have hard stops as described in the aforementioned patent they can actually also be programmed in in software today for example a yellow warning stop and then a hard stop for a buzzer with sound or a light for something to tell the person that they've gone far enough. Probably more likely is that the person hasn't gone far enough because of the pain involved in teaching the foot once again, and in this case again the making some sort of reward system or interest level and going the full distance that is needed, but to the doctor's advice is desired to also noted that the data about what the patient is doing can be transmitted instantaneously over the Internet to a person in a rehab facility so the person does not have to be present. Indeed for example someone can be doing the exercise in question on the battlefield literally, where the doctor being in a VA hospital stateside.

The illustration of FIG. 4 is also relevant to Wave exercise machines which shake the body, and make use of reflex actions in the muscles. One can alternatively consider for example the platform of FIG. 4b to be a wave machine that the person is standing on, generally grasping a bar like used on a treadmill. The games with hands and kicks and head motions can all be played with the invention using this machine as well It should be noted that the example of sensing of position and orientation of (and even identification of the type of) the barbell is just one example of exercise objects freely held and supported by a person whose position, orientation, or shape can be determined as part of a exercise or rehabilitation application of the invention. Another example is a squeezable foam ball having optically contrasting targets every inch around its surface (at least in a direction that would be seen by a camera), viewed by the camera as one undertakes some therapeutic distortion of the object, and sensed determination of distortion by the camera of the invention can provide both an input to a game, and be detected for teaching or compliance purposes. Another example is a stretchable rubber cord with contrasting ring shaped targets, which can be pulled like taffy as part of a rehabilitation regimen. Some examples of other freely held objects potentially moved around in space for exercise purposes are batons, pom-poms, small weights, and skip ropes. The Wii remote itself is also an example, for those wii games in which exercise is undertaken.

FIG. 5 illustrates a related form of embodiment including an exercise or other game for persons in chairs which also is relevant to simple devices used in the rehabilitation of injuries. As shown a simple exercise device 500 with movable resistant arm 501 is used by a senior citizen 505 seated in a chair 510. Because the person, or device or both are sensed, one can change the position and arrangement to suit the user and the particular exercise desired. And if desired the person can make gestures with the hand wrist target 505 (as one example) independent of the exercise which can be also sensed by the camera 515 and computer 520 of the invention, if desired in order for example to change a normal TV program shown on display of the invention 550 or control some other function such as ringing for assistance of a caregiver.

As one example consider that the camera 515 (and light source generally used for retro reflective illumination as described above) can determine the location of and to track the direction of view of the player in this or other embodiments by tracking the head orientation from the four or three target set 516 on the hat 517 of the player seated in the chair. This allows one for example to change view point of the displayed information, or use the head to for example control traverse of a gun in the game, or in a completely different context to point at an icon on the display. And the camera can sense such movement in both pitch and yaw, and can determine roll as well, tilting ones head from side to side. All these angles can be used to for example control an airplane on the screen for example, and can be played from a chair. The camera can sense the target datum 550 on movable resistance arm 501 of device 500 under the action of the persons hand 555. The arm 501 in this case is in the form of a lever coming up from device 500 from below. In the simplest case, the lever arm is moved back and forth and its position, extent of movement and if desired, motion path is determined. As before, a little game can be made out of it, which gives the person some feedback as to how far they pushed it how fast and how many times they pushed it. Words of encouragement and graphical images can be displayed, and anything else like can help make it more interesting. Indeed the pushing of the arm could be something that causes something in a game to be actuated.

The device 500 may also be considered to be a repositionable device for rehabilitation of injuries, for use by therapists or persons in their homes. The goal here is generally short-term repetition of a particular movement. Where the, the extent of movement and the direction may be very important variables, along with the number of repetitions. Then providing an easy way to readjust the device to a new position in order to assist rehabilitation or other exercise of other portions of the body, or the same portion in a different way. Key to this concept is the ability of the camera system to see machine portions to assist their set up. Portions can be targeted for example to aid their position and/or orientation to be determined by the camera of the invention (or another camera or cameras used for set up) and the computer may aid their repositioning by providing graphical or verbal instructions on the screen derived from camera based sensed position data. In addition after the machine is set up, the camera system can be used to recognize amount of weights or other settings and advise and record them and the machine positions settings used. Thus the machine of this type can be set up anywhere it is needed, and in any way required to undertake the exercise. Devices may be attached to chairs beds etc, wherever the patient is—also in a vehicle, a hospital bed etc It should be noted that as noted above, the warnings can be provided using the camera to advise the person that they moved the lever arm too far for example, or they are about to. Perhaps to the limit that they should these inputs can be put in by a physical rehab person or other healthcare worker rather than the person themselves for example, the limits can be displayed on the screen big warning labels big a voice can come on an image as telling them that it's, they should stop or back off. The image can be of the healthcare worker himself or herself or a friend or family member.

The PC 520 can be used as is known in the art to control a tv display 550 and provide sound to loudspeakers not shown, or to pick up voice commands from person 505 as desired and practical.

One can also use the camera of the invention to determine a pointing direction of ones finger as disclosed in the referenced patents and co pending applications. This is useful for pointing at objects on the screen for game or selection purposes for example. Or you can look at the screen and use the orientation of your head determined by the camera from target set to position a pointer on a screen-displayed object if desired. This, for example, may be used by bed ridden people or those confined to a wheelchair or a hospital bed.

It should also be noted that a trained medical professional can set up a particular form of rehab exercise this way. By using some repositionable mechanical device to particularly be set up to allow a patient who is in a particular situation to use the mechanical setup in a way that will help them perform a helpful exercise. Just as a device was located next to a senior's chair. It could also be clamped to the edge of a hospital bed for example, for persons who are in hospital. This case, the camera, and the screen can be located at the foot of the bed for example. And clamped to it thanks to the new modern flat-panel displays which are light, or a video projection device mounted in the wall can be used to project on a simple pull up screen located for example at the foot of the bed. Such devices can be used with most embodiments herein if desired.

It should be noted in the latter regard that in a machine may be adjusted in position in different ways one can also use the camera of the system and the ability to display easy to see graphic images on the screen to guide the user to set the machine up in the first place. For example you could show the user, a new arrangement of the machine on a graphic TV display. Then you instruct the user to move a certain physical detail of the machine (e.g. a arm) to a point in space relative to its center, that is determined from the camera. When the camera sees at the point is approximately reached that space It can tell the person to stop and lock it down there. The computer can actually depict on the TV display the positioning with respect to the center of the machine such that you can actually see when you're approaching the right point and not just hear a voice or other indication saying to stop.

The ability to help guide set up also leads to the ability to build new forms of machines. Even simple machines the only been require motors. In other words, one can actually set up a machine having let us say erector set like arms and other details. In particular positions that I might be good for a certain niche form of exercise. All of this since all of the set up can be guided this should be easy to do even in 3-D space. In addition, and a key issue is that the persons use of this machine is also monitored. So that if there is anything about the actual device that that might mean some sort of cautionary aspect with respect to extensions or particular banding or weights or any other aspect these can all be pointed out to the user on the screen and monitored in real time for help. This aspect basically allows one with relatively limited mechanical equipment to create whole new forms of exercise, where the resistance is formed either simply by hydraulic or mechanical springs or weights on pulleys, compressed air or other means. Because one can reposition the arms one can also fold the whole thing up and get it out of the way it is for example in your bedroom.

In another version you follow with your hand or foot the path displayed on the screen, such as a straight path or a curvilinear path, in order to undertake a specific type of rehabilitation movement in this case with the person's foot having target on the toe 570 which may or may not have resistance associated with it. A 2D or 5D path can be monitored and/or displayed with the invention. Also one can sense the extent and orientation of movement and even the path if needed or desired. This is unlike the Wii device of Nintendo, which can be faked easily, as it uses acceleration rather than actual movement for many of its functions.

The invention can allow a built-in training function to be provided to where some of the feedback to one might get from a personal trainer in a gym can be provided in the home through computer programs. This can also be used to train persons in performing rehabilitation exercises.

For Seniors and others who nostalgically remember old movies, the displayed information can be composed of video clips from same. These (or any other video clips) can be pieced together to form a simple game for example. If the player/viewer wants the couple shown to kiss, she can move her head (as one example of a gesture or expression which can be used to trigger an action of the computer system) toward the screen, which movement will call from ram memory an immediate clip of a couple kissing—which might even be taken from another old movie. This same sort of thing can be done with sports games, where your physical motion signal causes some action to occur, such as a hockey forward taking a shot at goal. Voice signals might also be used.

Figure 6:
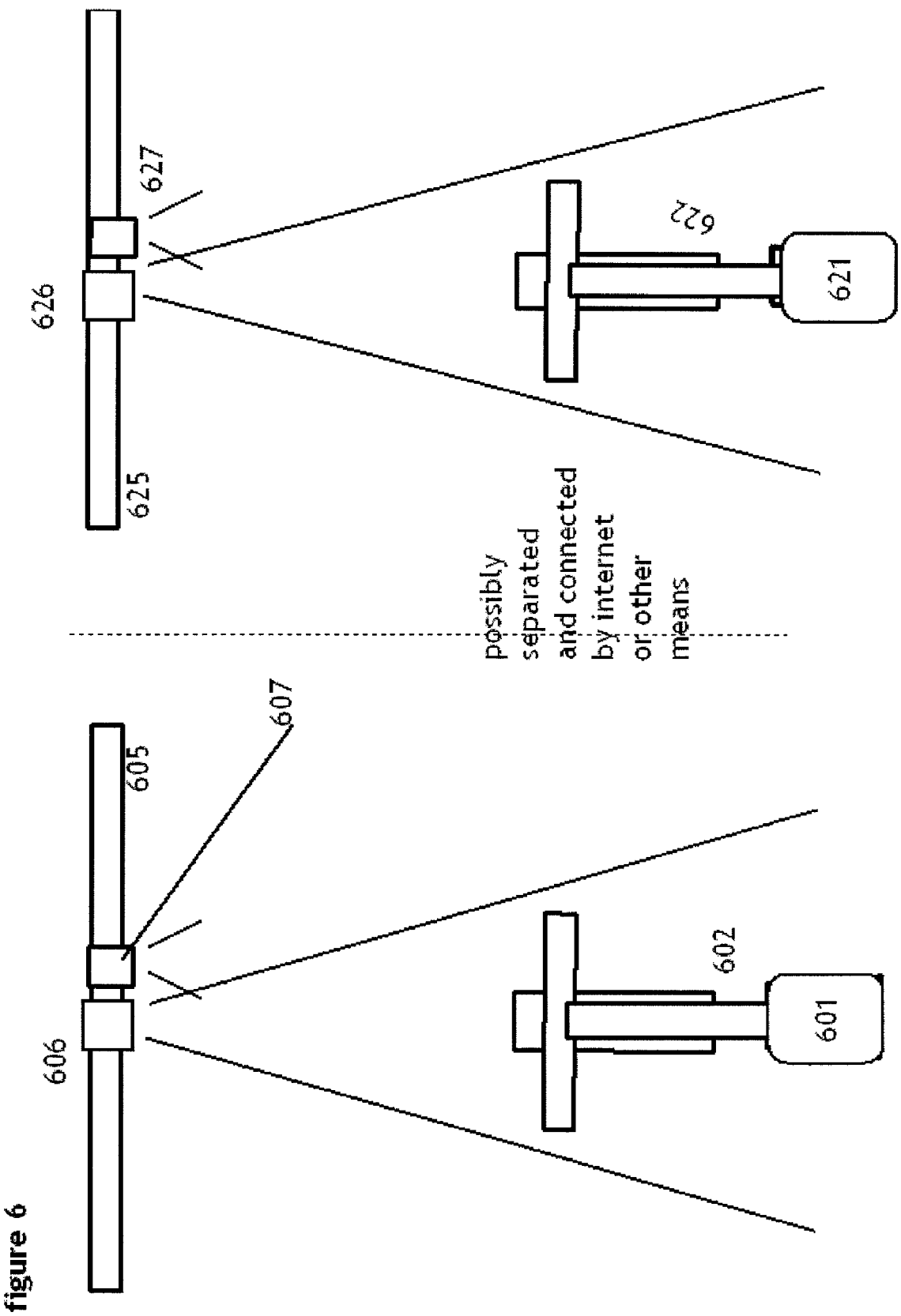
FIG. 6 illustrates representative social embodiments of the invention. Further illustrated are methods and apparatus to control an avatar of a user or someone in a social networking site or other venue and where desired to incorporate this function into a game involving exercise.

FIG. 6 further illustrates representative exercise based interactive social embodiments of the invention. As has been pointed out above, the invention can be used to improve social functions and stimuli and therefore motivation to the user. This in turn. When connected to exercise motivates them to do more exercise, which has huge benefits to society as well to themselves. Let us now consider the spinning class of FIG. 1 and to make this more fun and bring it up to date in terms of today's possible Internet interaction abilities, let's consider a particular case, where there are two players, Molly 601 is on exercise bike 602 in front of the display 605 and IR sensing camera 606 (with included light source) and web cam 607. The computer speakers and other aspects of the invention utilized are not shown for clarity in this example. Molly, using the Internet facilities such as Skype or other such webcam type services, has called her friend Judy, who is in another location, and invited her to partake in a spinning class with her. Judy 621 is on exercise bike 622 in front of her display 625 and ir sensing camera 626 and web cam 627 and computer likewise not shown. In this particular example, Judy and Molly can each see the image of the other on their respective display screen. (And in some cases, such as in a gym they could be physically seated side by side, but in this case they are remote from each other). For example, Judy's image is shown on Molly's screen 605 in real time due to the normal use of a Webcam and Internet service. Both Molly and Judy can ride their bikes according to the invention and their data in so doing can be displayed to them, and if desired to the other(s), as well as the video image. To illustrate further capability, In this particular case, however there is a third person shown on both their screens, and that is an image of a spinning instructor, be it real or virtual This instructor can be presented in three forms at least. The first is a live image of a real spinning instructor instructing both of them and it is realized that there could be more than two people to instruct—indeed there could be a class of 20 or 30, or 3000, although there is only so much feedback and instructor can provide to individuals as the class gets bigger and bigger. Nonetheless, the instructor could see let us say see 20 different images of persons in an internet held class on a big-screen monitor at his facility and be looking at them just as he would in a real gym Or he could be looking at the data coming from them picked up by the cameras and see how it is between norms to having the images preprocessed for example to present to the instructor. It is noted that one could actually combine and have a live spinning instructor whose video appears on everyone's screen, and then assistance could be done by the computer analyzing the positions, heart rate, or any other data from the person and in feeding and information individually to them.

Another situation is to have a completely computerized instructor in which no human instructor exists at all at the moment of the game. In this case is image would be either pulled from video clips of him giving the actual lesson or generated using animation from 3-D graphics, which are more adjustable to react to particular moves that one of the players might make for example if Judy did something really unusual. It's also noted that graphics and other clips and other information or data needed could be downloaded from the net in a huge array of possible variations. Indeed, one could choose one spinning lesson from may be a thousand spinning lessons provided on the net from different countries and different languages in different modes and so on. This also could lead to new forms of exercise equipment which could be adjustable in different ways also to fit a variety of instructors, languages and systems that could be done.

in any case returning to the social issue it is felt that by having Molly able to engage Judy to spin or otherwise perform exercise, whether that it increases greatly the motivation of Molly to a can presumably Juty as well to undertake the exercise, the overriding goal. It's much more fun to exercise with a friend, and it's much easier to do so from ones home than it is to go to a gym where you're not only have the effort of doing that but you also have certain social situations that perhaps you might want to avoid or the equipment is tied up or its snowing outside, or whatever. One of the advantages again of this whole system is that if you locate the device in your family room or bedroom or other room as you normally would, you can use the TV and Webcam and computer all for other purposes when you're not engaged in exercise. Thus the incremental cost is small, above the base exercise machine or device itself.

Optionally the machines themselves may be able to be modified using this invention. For example, let's take again the case of a bike which typically has a brake on the front wheel engaged by pulling a lever. The position of the lever can be sensed by the camera and as one puts more and more force into the pressing of the brake pads against the wheel using the lever of the handlebar the camera computer system of the invention can sense indirectly and crudely the amount of force and thus resistance being applied to the wheel. This information could actually form part of the game where for example a spinning instructor says go to force five and you would can pull your own lever to that force, the display of force being presented by computer on the screen in front of you. The possibilities are endless, because the screens can be large and able to have a lot of data displayed as well as provide large images of your friends who are spinning with you so that you can have a feeling that you are indeed in a real fitness club, if such is desired. The computer can also be used to track progress, and relative progress (which could involve more than two people).

While spinning is something typically done by a younger persons today, the idea of social exercising as just described is not necessarily so limited. Similar motivational approaches disclosed can be used with seniors for example 80 years old doing exercise with their friends. However, the machine itself, either its type or its design or its size or other factor, may be less strenuous, with less impact or the like. One could almost even be the same program just scaled back in terms of the settings for how fast, how far, how much resistance and so forth. Perhaps with older persons, you would have an older instructor, who might tell particular stories the related to do them the music that one played could be 1950s songs as opposed to todays. Ditto the background images to one might use And so on. This latter aspect has another interesting possibility in the sense that one can use the availability of such a program as an outreach avenue from a retirement home for example, that might wish to help people who are currently in their own homes, but eventually would move into the retirement home. In this case the exercise activity could be at accompanied by other sorts of things such as health assistance, meal management assistance, and the like.

It should be noted that as before, the camera/computer system of the invention can be used to score the players. In other words, Judy, could have made more rapid moments higher movements, and so on in which case you Judys score might be construed to be higher than Mollies. And there could be handicapped given for various reasons to the players as well to to modify their scores. Such a scoring ability can be done dynamically almost so that you can see that you might need to catch up by cycling faster toward the end of the session much as you might in a normal a race for example.

The above may be envisioned as a forum for social interaction of a person typically in their 20s or 30s who enter acts over a social networking site for examples such as Facebook. In this scenario, the person might look up 5 of their friends on face book and query if any friend wants to spin? Let us one or more of the five would then say yes, and the group thus formed would form the spinning class so to speak. If one other person was present in the group besides the initiator that person's video image could be displayed on the screen of the initiator. If more than one were present each person could for examples see the images of all of the others. These images could be arranged on the screen as the person might choose. Perhaps one image larger than the other perhaps one image Central and the others around it. And so on. However, because spinning engage as an instructor who guides the class is clear that one would generally wish to display the image of the instructor as well. But this invention does contemplate that one could have a class or the instructor simply was a voice (and musical accompaniment generally) conveyed to all.

For example, if Mary as participant number three for example is not raising her hands high enough. This would become apparent to the computer program which could compare her hands against a norm. That is the height of her hands above the bike that can be determined. If one has a datum on the bike such as target 53. Or one can actually teach relative position aspect as a first step in the in the game, where Mary and all the other participants would raise their hands over their head to the typical highest point in the camera would simply record for each what was relative to the baseline of the handlebars or other chosen point such as 53 or 54. Thus taught, the system simply runs a comparison against that maximum point to determine whether the persons raising their hands high enough or not when the instructor queries.

A data table can be made up, which is taken with the camera at each of the three participants Molly, Judy and Mary computer in this case looks at the data of each compared in the position to be taught value desired such as a maximum value and determining the rotational speed calculated by comparing subsequent frames In this particular one snapshot of each of the participants is clear to Mary's hand position is clearly less than her optimum high. If the instructor has as its in this case, the case asked the adjustments to raise their hands high. It would be clear that Mary is the one of the three participants that has not done so. Therefore the program seeing this it difference can save Mary you're not even close or Mary you've got to do better or other such comments. These can be chosen randomly from a library of such comments relative to hand locations and simply the names interchanged. If it's for example Judy rather than Mary, whose hands are not high enough in the air. Note that this approach can be extended to other activities too, such as sports, ballet, dancing and the like Let us now consider an almost completely opposite set of persons, namely, a senior citizen Mrs. Jones 80 years old, who wishes to interact with one or more of her friends in a similar manner to do a simple arthritis exercise with her hands. Because she has trouble walking as do one or more of her friends, she might be seated in a chair and engaging in the activity as shown in FIG. 5. she might find her friends through an interaction internet site perhaps run by the Arthritis Society or a rehabilitation group. In any case, having found two of her friends to engage in the activity, they go ahead and do the exercise just like the spinners above. An instruction program may be provided to tell them how to perform the exercise by moving their fingers in a certain way. This program could be either provided by the Arthritis society or in a data base from the Google Open social site as mentioned or could be on a DVD or any other medium appropriate to the task.

In order to facilitate operation of the invention, Mrs. Jones might advantageously employ a retro reflective ring on her finger as disclosed in my previous cases Or she might have a ring on her thumb, or a targeted thimble, which would facilitate sensing of relative position of her finger to forefinger, to determine a pinch motion. Or she could have rings on two forefingers, one hand to the other.

Now let us consider an extension of this idea to actually aiding a person such as Mrs Jones to regain a lost skill and thus gain much enjoyment.

Figure 7:
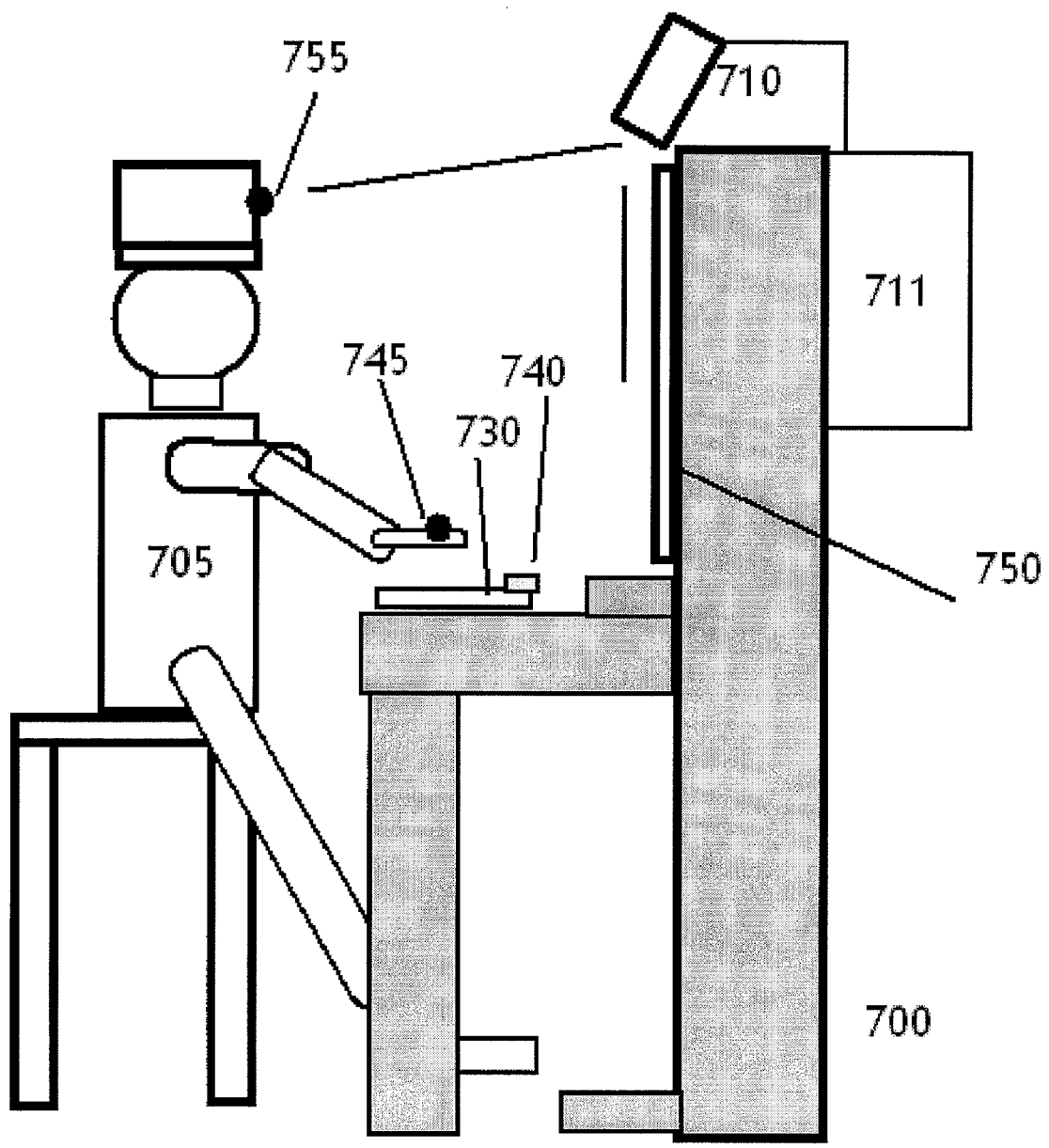
FIG. 7 illustrates an aspect of the invention to help arthritis sufferers and further to help them regain some degree of their former abilities

For example consider the piano 700 of FIG. 7, being played by a person 705 with arthritis who cannot now bend her fingers enough to hit the keys properly. Camera 710 and computer 711 of the invention determines her finger position and the computer 720 calculates the location and if needed, the trajectory of the finger in order to determine which key such as 730 the person would press with their finger 731 on the piano—if it could comfortably hit the key in the first place. It then causes the computer to call a wav file and drive a loudspeaker 735 to produce that note. It is generally possible to see finger location relative to the keyboard fast and accurately enough with no added target, but one can be employed, such as target retro reflector 740 on key 730. Nail polish such as 745 or rings or other such contrasting objects can be used on ones fingers as disclosed in many of my patents and applications.

The piano in this example is further equipped with an optional LCD display 750, ideally running the length of the key board. This can be used to provide a graphic showing a person who does not have innate piano skills, where to hit the key in order to play a note of a given song. This aspect is not limited to persons who cannot hit the keys, and may also as an instructional too. When a person's finger has hit a certain key, the graphic can then move on and show the next note, building up the song as it does. This music can also be recorded by the computer or transmitted as desired.

The LCD or other display 750 can also provide an important function, namely presenting the music to be played, and then making the pages be "turned" without straining the player, either by the person moving their head, perhaps using a head target 755 sensed by the camera or seen directly by the camera without need for the target, especially since the motion is slow. Another aspect is that since the computer knows what key was last hit, when this key is at the end of a page, it could be automatically turned, assuming the music was synchronized with the keystrokes. This same idea can be used for typing keystrokes too, for those suffering from disabilities, possibly supplementing voice inputs of words.

FIG. 8 illustrates an airplane game embodiment played on a treadmill A modern-day treadmill used for exercise in the home or a gym has a motor which drives a belt that you walk out the motor essentially moves the road under you and you have to keep up with it. Naturally you can dial in whatever speed you wish the keeping up part allows the device to calculate with accuracy how many miles you are walking, and imparts a rhythm to the exercise The provision of a motor on a treadmill has a disadvantage namely that it creates a safety hazard. This is why there are kill switches on most treadmills with big red push buttons or safety chains. This being the case it is hard to make a game out of a treadmill other than a walking game where you might steer (using your hands in the air or optional handlebars for example) something through by a roadway or city such as I've disclosed in co-pending applications. It is not easy to use ones hands in a situation like this however, because you need to keep up with the motor, and should for safety hold onto the bar. One of the big arguments for a motor is to facilitate calculating your travel, since speed and incline if used are known by the machine. But a motor is not required and many passive treadmills have been built. This sort of treadmill, like the exercise bike can provide a safe and fun platform on which to build games to inspire people to get their exercise. And the invention can track the person's movements and calorie burn, without having to have a constant speed (for a given setting) motor driven belt. This means the person can stop, start, and even move backwards and still make this calculation.

In this example, however at the goal is to simply have a walk, in some cases perhaps against minimal resistance. One can while walking do other things such as use ones hands to perform exercises, also as part of a game. If the treadmill is large enough one can be walking and even go side to side a bit. With sensors and no motor involved, one can even skip or do dances or other things that could involve even going backwards for a few steps if the game called for it. In short, one can make a game out of doing many sorts of movements, all the while walking in one's family room or other location.

The invention can determine location of object features and can feedback data to a person relative to their actions. If they go backwards as well as forwards this can be sensed in the z-axis (longitudinal treadmill axis) using either the angled camera trigonometric approach of FIG. 1*d*, a side mounted camera such as 51 in FIG. 1*a* above, or stereo photogrammetry or other 3D camera methods from a front or rear viewpoint.

Consider FIG. 8 which illustrates a person 800 playing a video game such as an airplane game, (eg flight simulator or top gun or the like) while walking on a treadmill 810 having belt 811. In this example, the speed of the person driving the treadmill by walking on it at different rates (determined for example by tracking targets on the toes of his shoes 805 and/or 806, or alternatively, ankle band targets 807 and/or 808) chosen by the user or the program to control the speed of the virtual airplane displayed on the screen and the yaw of the plane is determined in this example by ones wrist positions up and down in the vertical plane, with the fully extended arms representing the wings of a plane which is. Wrist targets 815 and 816 are used on each wrist of the player 800 to allow camera 820 processed by PC 821 to acquire the data as to where the wingtips 815 and 816 so to speak are. You could dive down and raise up in the pitch direction by bending over or raising up your body, and this movement can for example be sensed by monitoring the position and/or orientation of hat such as 830 with a 3 target set facing the camera, or alternatively by determining a drop in position of the wrists in the y axis. As a further alternative the y axis position of a collar target 835 around the neck or other suitable target could be used. Or one can use natural features of the person, with no artificial target at all in certain locations, or even in all locations desired, if the image acquisition was reliable and fast enough in normal room lighting to determine the degree of bending over, or the angulations of the arm positions to control the plane. The treadmill allows forward motion of the plane to be controlled by simply walking at different speeds. Resistance of the treadmill can be adjusted to suit. If an incline is used or in general, the belt 811 can be prevented by known means from going backwards if desired. It should also be noted that with suitable internet bandwidth, image processing of camera 820 could be done remotely at the internet server 870 rather than locally on PC 821 for example.

The invention can be used for the diagnosis and treatment of mental, behavioral and other disorders. In addition, the invention in a related manner also contains novel methods helping the mentally ill and other persons improve their quality of life. In the area of mental disorders for example, the invention can be used to provide a digital 3D model of a partner on the life size projection (or other) TV screen of the invention. This partner can be programmed to carry on a conversation with the person (who is often lonely and needs someone to talk with or dance with, or do something else with), with the dialog done remotely over the internet (for example by psychiatrists, physiologists or other medical professionals, or from pre recorded video clips from DVD storage say, perhaps in response to questions asked and recognized by voice recognition software such as IBM Via Voice. Alternatively or in addition, the body model of the user can also be displayed on the screen, such that the dialog between ones self and others (which could be many) can be observed in the third person. The model on the screen, which could be of another person, or the user, or both, can for example dance, in tune with music, and this can be a dancing partner for the user. Dance therapy of this sort is often valuable for persons who are ill and often alone.

To effect animated activity of this sort requires more powerful computers since the whole model (or significant portions) needs to be changed dynamically, which is computationally intensive where 3D models are concerned. A Pentium 4 with 3 GHZ together with a high quality ATI or Nvidia graphics card. However one can do this job with simple 3D models. Tai Chi is also possible with the invention in this mode, and does not in general require the response speed that dancing does. To make the tai chi session meaningful, harmonious sounds and pictures. are displayed One can in FIG. 4*b* consider that the weight lifter 450 without the weights is engaging in freestanding exercise game taking place in front of a large display, in this case a dancing game for seniors or persons who might wish dance therapy. In this case the dance "partner" is a substantially life size depiction on a display such as a vertically positioned RPTV or plasma display This arrangement can be used for other games, such as a quick draw game discussed in my co pending applications, and does not necessarily have to be exercise related.

The dancing person can for example, be dancing or talking with the model depicted on the screen. The model could be that of a family member, a friend, a doctor or whomever. Or with an animation of a famous movie star who the person likes. This interaction could also be done in the third person, with the model of the person also depicted on the screen and having a conversation or dance with the other model. In this case it is generally necessary to sense the position and orientation of the person in order to manipulate the image of the model—or the person—on the screen. It might however be therapeutic to have the image driven by a computer program, which would cause the person to then say words in response to what he saw his virtual self doing. For example, making a social error. This can be part of the therapy itself, which can include teaching functions to help the person learn to better participate in social activities. Or in a pure dance context, how to do a particular dance step.

One can provide voice or responses via the computer or remote manipulation of data and in turn store the response of the patient both voice and movement for later diagnosis. In undertaking interaction with this system, the images and sounds can be specialized to help stimulates one mental activity, particularly valuable for older persons in retirement homes. For example one shows an image on the screen. You can move your hand or your head to either it look at that image or to try and touch it or indicated by pointing or other methods. These images could pop up at different points on the screen and you go ahead and do that. Certainly you have to bring your brain into view at the response of your brain is indicated by movements of your with body parts that are sensed by the camera again words of encouragement can be provided or you could move onto the stage to or something like that. Some of these things could get involved were willing objects going across the screen were moving and edit when they were doing certain things in their moments. Then you had to to this. This sort of activity could be used for multiple purposes. One is to train someone a second purpose is to help them use their brain facilities, particularly an issue for older patients and a third would be for general amusement One can also do this in conjunction with other people. In this case, you are essentially doing that particular activity with respect to the someone else doing the same activity that someone else given the invention can either be sitting next to you can be in another room of the same facility or could be across the world. Importantly, the person could be a family member, and in the video context shown in FIG. 6 of having video of the person as well as playing a game. This would be true here to and perhaps even more useful for keeping in touch with your family while doing something that might be in one way, family fun and in another way, a helpful exercise for one's brain.

A useful aspect of the invention is that it can instruct people in how to relate to social situations. This is particularly a problem for the mentally ill, who are often an extreme disadvantage and in the end become paranoid of social interaction. The invention can help them in their home to learn the skills needed to go outside the home. Just as noted above, one can use the TV camera to monitor the position of hands heads and other parts of the body, and we realize that in many cases these positions and movements are actually part of the social interaction. We can use the camera to diagnose whether these movements are correct in response to standard norms of images and voices that are presented on the screen and thus determine with analysis if certain illnesses are present. But we can also use them to help guide some sort of rehabilitation training in this regard. This can also be in response to those persons who have been injured in accidents and don't have full possession of either physical or mental faculties. The exact forms in which the video and audio information will be presented on the screen from the computer or from a live remote source or both depends on what treatment is required. The key here is that the ability to have an input with both the voice and the physical positions of the patient is desirable and available using the invention at a price that can be afforded in each home, where it really a lot of the treatment has to occur both for cost reasons and for personal safety and embarrassment types of reasons.

The use of the camera on the display or nearby allows you have interactive video sessions over the net, and to further incorporate such images in diagnosis—especially for remote diagnosis. The regular webcam like camera functions can be turned on if desired when some sort of non-standard behavior (manifested as movements, positions or voice for example) is detected.

I feel the invention may even be able to perceive subtle differences in mannerisms and expressions, with appropriate software to analyze motion gestures and further facial expressions as known in the art. Many things of interest are manifested as head positions hand positions etc. which can be elicited in response to stimuli on the display or audio ally in order to identify some kinds of mental disorders at a far earlier state than one might do it today. In particular those disorders that come out in a social way that is difficult to diagnose with children. If they are not quite learning the social skills properly in the early years, it is very difficult to tell normally speaking. But if there is a medically large amounts of video positional and voice information in response to known stimuli that the instant persons activity can be compared to, then there is a chance to do this and the payoff is to make a much better life for the person in the future via diagnosis and early treatment As one example of coding of targets to help in tracking feet with one camera during complicated dance steps or other types of motions, one can have a pair of shoes with retro reflectors on the toe and heel of each, which optimally can wrap around the toe and heel so they can be seen at any angle. The toe can have vertical stripes of no material while the foot has black dots within the field for example. The right and left foot can be coded with respect to each other as well, if required.

It is also possible to provide targets or other features seen by the camera system of FIG. 4 that can see on object underneath the feet of the person such as a rigid or semi rigid platform 480 with targets 482-485 allowing the position and orientation of the platform object to be determined, and intern movements in it which could relate to particular dance or exercise routines. This would not be used generally speaking by persons such as the weightlifter shown in the figure.

The example of FIG. 4 also serves to illustrate what could be a sports game, with figure such as either catching a ball thrown, or throwing a ball. This virtual ball could be thrown at the TV set, sensed by the camera and a 3D display at the remote location present this ball to the other player to catch. This is not like some of my earlier work which showed throwing real balls (or hockey pucks or whatever).

As disclosed in previous applications one may devise a game in which the person on the screen may be playing directly with you without the use of an avatar in the virtual world sense. An interesting game can be played with a baseball pitcher pitching a ball at you the catcher, holding a mitt that is targeted (or alternatively you could be a batter with a bat). The goal is to catch (or hit the ball). The mitt or bat can be seen by the camera in up to 6 degrees of freedom, and the result of your movement in response to the display presented. Either visually or audio—Like "yer out"!. A DLP rear projector may be used which can present the image in realistic 3D for example. The screen is most realistic if it is life size in the vertical direction to give it the most realism is a picture of a picture and a dynamic video the pitcher throwing a pitch which I the catcher and to catch this can make a whole game for the child that causes him to move around at least within a limited space such that it could be done in a bedroom or living room or somewhere. Similarly the player could be a hockey goalie, with a targeted stick to assist the camera if needed. And the experience doesn't have to be sporting goods equipment or sport related One could pretend to be a wizard in the Harry Potter movie, waving a magic wand around, said wand tracked by the camera and the data there from used In order to perform tricks on the screen.

The invention with its sensing and feedback of information provides numerous advantages, among them an ability to determine a users performance and via a computer program make suggestions or track the performance or see if it is within bounds, or suggest deviations to make it better. It can also send your performance information to someone else over the internet or other means in order to compare your data to theirs, to drive an avatar or other representation of you, or to diagnosis remotely your actions. By combining sensed data, with actual webcam gathered video images a complete experience and informational base can be developed.

While one can use a stereo pair of cameras or other means to get 3D information as disclosed in my previous applications, in most cases we are trying to keep the cost low and the system simple and robust. A simple single camera generally will do the job which is sufficient for many games Even where this single camera is a new 3D time of flight type, like those of Canesta company or 3DV systems company, the use of specialized retro reflective target points is advantageous to help rapidly located the points to be measured or tracked. Here too other of my previous inventions are helpful in that you can use the artificial target to locate one or more regions to be tracked and then use natural object features to determine other points of interest within a region.

Another point to stress concerning the invention is the fact of the performance of multiple functions. This allows it to be shared amongst a large number of different users and different uses for the same user and with a commonality of function, the familiarity with it's use, and so forth.

From a cost point of view, it is clear that the same computer, display, and camera system can be used for a variety of applications, thus making the incremental cost of the invention herein relatively in expensive. Indeed the screen (the most expensive item, typically) can be used for normal TV show watching or internet activity as well, or for control of the home Many people already own exercise equipment they don't use because its is too boring.

As stated above, an important point of this invention is to stimulate people to do the exercise itself. When you tour people's homes or fitness facilities in rest homes or mental health facilities or other places you see bikes, treadmills and other exercise equipment but almost always unused. It's clear that most exercise equipment is only used by truly dedicated people. And that's the problem how to get more people to use the equipment? In order for this to happen the equipment has to be easy to use and it has to be fun. It has to give good feedback, and it has to be at the right price to where you can have it in the locations where people will naturally tend to prefer to use it. This again is another focus of this invention because the goal here is to keep the price low so that people can use it in the home and not just in a gym or institution. Indeed some of the features of the invention allow a built-in training function to be provided to where some of the feedback to one might get from a personal trainer in a gym can be provided in the home through computer programs.

Method and apparatus have been disclosed in co-pending referenced applications. for improving the likelihood of success of a given health plan by prediction of future appearance and providing an ability to monitor the movement and shape of the user in order to tailor the plan, and the video or other instructions and stimuli given the user to suit the situation. In any of the games above one may make a part of the play, the projection of your appearance in the future as disclosed. For example, a person playing the game could see themselves in 6 months time, if the kept on as they are doing. If the person goes faster, or works harder, they expend more calories also in certain places depending on the exercise type, and variables such as these are inputted to the machine. It can be competitive as players can see how much they can look better. Also other predicted effects like overall weight and endurance can be displayed, not just images It is noted that a sensing laser scanning projector or laser scanning detector by itself as disclosed in my cases filed in august and September 2007 is able to alternatively sense the points needed for this invention, and has and advantage in ambient light rejection, if this is a problem. Such a device, in projector form, can be operated from the rear position 50 and used as well to project on a screen if desired.

The invention contemplates optional display of the digital model or a real image of more than one person side by side for example:

You and a friend

You and a plurality of friends, the others remotely located with data files transferred over the internet or otherwise You and yourself from a stored image from an earlier time.

As noted in my August 2007 filed case, I mentioned that one can interface a monitoring device to the person and interface this to the computer 25. for example, pulse rate monitor transmitter 35 or the pulse monitor of the handgrip of the bike (not shown). Wrist bands or other body hugging devices used as targets can also serve as pulse monitoring pickups for such purposes, just as other body clothing can also serve as targets. The same can be said for bud type or other earphones from an IPOD which can have retro reflective tape or corner cube retro reflectors on them such that each ear can be seen and head location and angle in the horizontal plane determined by the camera and computer system.

It is also noted in the regard of monitoring a players positions and exercise via the camera computer system of the invention, that criteria can be set up so that a player doesn't don't get certain powers or other benefits in a particular game unless their motion or extension of their body or other aspect of the exercise meets certain goals, such as speed, extent, etc. rotation Another factor could be the integral of their motion over distances or other factors proportional to Energy expended, which could if desired be then translated into "energy" of their game object in the game, and so forth. Such criteria are a powerful motivation to keep exercising, particularly in playing against others. Because of this, it is desired to monitor heart rate by the PC 25 via what ever practical means, and make sure healthy limits are not exceeded, providing warnings to the player if there is a danger thereof.

It should also be noted that the one can display on display 24 the results in 3-D stereo for example using "Crystal eyes" or other synchronized glasses and a DLP projector running 120 Hz to provide 60 Hz alternate views to ones eyes. This then provides even more interesting exercise potentials in that you can react in "Z" or range axis to stimuli coming from the screen in that axis or apparently in that axis. This reaction can be using limited Z axis capability as taught in FIG. 1c using single camera photogrammetry or using true 3D camera sensing systems such as via binocular stereo photogrammetry or time of flight related systems such as that of Canesta corp.

The invention, by monitoring the motion of a person on bike or other exercise machine or jumping around may use this information to calculate caloric burn rate, which may be more involved than just monitoring resistance of the bike wheel for example, and its velocity (though largely dependent thereon).

Using the invention you can input your goals via the computer, or via voice recognition or other means. Also could handicap yourself relative to others and the display can be programmed to show the goals entered, relative data to last session or others. Or projected value or images at some time in the future if one continues x times per week. One may also display instant rates; instant heart monitor if pulse or other measurement interfaces The computer can be programmed to provide you an instruction if you aren't meeting goal in stretch or rate or other exercise variable. Also can, in a game, play those in your level or handicap yourself with respect to their levels Competition is a major motivator to keep exercising. And this is much more fun in a social setting against someone seated next to you (eg in a gym) and is still neat over internet. If you're playing a game and you start to slow down your rate of pedaling the bike for example, the game could be programmed for you to lose points as a result. If your energy expended in the game (calculated from factors such as integrated movement, resistance, pulse rate, etc) for example began to taper off, an energy bar depicted on your screen could start to go down. The energy bar could change size or color or any other variable desired. And it could be compared to your competition on a bar graph on the screen for example. Energy related data can be calculated from machine variables extensions of the persons body in the exercise or both or any other factors. The invention can be used with multiple machine types and games little or no hardware cost, without wires running on the floor or other hazards.

The camera of the invention can view retroreflective datums or other features on ones shoes and other parts of your body, both for position and angle, 30+ times a second with good accuracy at low cost—assuming you use special targets either built into the shoe toe and heel, or side, or to into clothing or attached to the person or clothing, for example with Velcro. Dual core/quad core PC computers today can process the camera information concerning artificial targets or in some cases natural features on a person or machine at the same time they drive the graphics. A viable dance experience and training can thus result, and one can dance with a virtual partner or teacher, using a big screen HDTV turned with long axis vertical so that the image appears life size or nearly so (for example approx 55 inches in vertical direction)

It is noted that the means of using portions of your body to enter data into a video game can be combined with other means, including conventional means if desired. However the exercise advantages lie in getting your body involved in playing the game. Various movements such as raising up in the seat of a bicycle, or pushing back at something coming at you (especially exciting with a 3D display such as Texas instruments DLP projection TV provides). The computer can allow you to enter your goals, verbally using voice recognition or with a keyboard or other means. You can also handicap yourself relative to others who may have disabilities or be less skillful. And you can use the computer to predict an outcome of continued play and exercise. In addition you can make in software criteria that your game action is only entered into the game if it is correct, or of sufficient speed or magnitude. For example if you raised your hand high enough. Alternatively if you don't, the entry into the game could be decremented in order to inspire you to do better for example. As noted above computer analysis of the camera images can determine the "quality" of the movement, not just the extent or duration. For example one might define in a given exercise quality as a path taken and timing Another application is that the game can show you on the screen what you are to do, and then you are given a certain time period say to do it, or judged on the quality of doing it, or both.

The invention thus have in many cases intuitive physical hand body or leg responses to already existing video game graphics designed for conventional game controllers—a big cost consideration as the exercise market is at the moment much smaller than the video game market. The camera of the invention can be used as well to make a relatively crude face scan of the player, allowing facial graphics to be entered into the game.

It's noted that in Italy or hands gestures are widely used. One can make games that utilize such hand or other body part gestures in the games, including social games where the hands gestures are part of the social interaction. Note that the exercise gamer could optionally use his or her hands to signal the TV and computer, in the same manner as a remote control.

The invention can be used to check for anomalies in activity vs standard norms, or versus previous play of the same person. This can be used in some cases to determine if the persons health has degraded, or they are off their Medicine say (for example manic play of the game, or alternatively lethargic). It may be possible to identify signs of oncoming (or recent) psychotic episodes to allow timely and mental health intervention. Abnormal responses can also indicate that a patient has taken too much or too little medicine. If the game can help monitor this, it may be possible to actually reduce dosage, also because of the value of physical games such as the invention in countering depression and mood disorders.

The speed, magnitude or other movement variable in the game computer can be scaled for different persons. Seniors or injured people would not be expected to move as fast or as far or perform the complicated movements that others might asked to in a game to get a good score for example. The speed or magnitude to create a response can be scaled in a computer such as 25 for example. However, in the game itself, the response time of a bad guy say to ones movement may be fixed, if the game software is already written and not software changeable in the computer. It is expected that in time, software code from game companies will allow for variations in timing and other variables to suit exercise based games, and further will allow code to be enhanced where physical or cognitive responses are desired to stimuli provided by characters or events in the game. However today, the games are not this way. Where timing is a problem, one can use a predicted motion of the person doing exercise, to trigger a game trigger. For example, if one in an exercise game is to swivel a virtual gun by moving ones hand to full extension leftwards, this cannot be done as fast as someone can move a gun by pressing a switch on a D pad. So to get the same speed, we can monitor position and velocity of the persons hand, and determine what their eventual position will be, and use that data as input to the game. Or we might just choose to use velocity itself. The faster you begin moving your hand the more the gun swivels, or the faster it swivels. Or whatever else you program. In this manner one can approximate the response time of the existing video games while still undertaking movements providing worthwhile exercise. In some cases change in velocity, acceleration/de acceleration could be a variable to use. As camera frame rates improve, also helped by strong target signals, the ability to determine velocity and change therein improves as well.

It should be further noted that another way to use conventional video games designed for conventional game controllers, is to provide optical inputs for some functions that are not timing dependent in the game program, and use the game controller for the rest. This requires typically the user to stay more still and get less exercise, if for example the controller was attached to the bike of FIG. 1, and only left hand movements were optically sensed say, leaving the right hand free to operate some functions of the conventional game controller. It is possible though to consider another version where very fast commands could be given (eg a trigger shot) by voice or with a wireless switch held in one hand, which can be operated even though the hand is moving during exercise.

The invention's combination in many embodiments of determining location or orientation of both portions of persons and objects allows better combination of many exercises and games. For certain niches may be the only exercise device a person will use—a completely un-served market today and also perhaps those most in need. (Disabled persons, certain seniors, etc). The social aspect of the invention may aid this greatly A reason for purchase of the exercise system of the invention is major improvement in motivation and fun, with much more capability and information provided, without much added cost—and perhaps no added cost in some situations where high cost components such as the display or computer are justified by other uses (eg watching TV or surfing in ones family room or bedroom). Indeed for high end models, one can possible argue less cost if the exercise equipment would have had a fancy control panel not needed with the invention (which panel can be replaced by the computer and display for most functions).

While the invention has been described in connection with numerous embodiments, it is to be understood that the specific mechanisms and techniques that have been described are merely illustrative of the principles of the invention, and numerous modifications may be made to the methods and apparatus described without departing from the spirit and scope of the invention.

The invention claimed is:

1. A computer based exercise method comprising the steps of:
   providing an exercise machine on which a person exercises, wherein said exercise machine resists the effort of said person when exercising;
   providing a computer and a computer-controlled video display for viewing by said person;
   electro-optically determining data concerning a plurality of points on at least one of said person and said machine;
   processing said data to determine a variable related to one or more of said points; and
   using said determined variable, controlling a video game program in said computer.

2. A method according to claim 1 wherein a tv camera is used to make said electro-optical determination.

3. A method according to claim 1 wherein said processing is performed by said computer.

4. A method according to claim 1 wherein said processing determines the location of at least one point.

5. A method according to claim 1 wherein said processing determines the location of at least one point relative to another point.

6. A method according to claim 1 wherein said processing determines the velocity of at least one point.

7. A method according to claim 1 wherein said processing determines the acceleration of at least one point.

8. A method according to claim 1 wherein said processing determines the location of at least one point.

9. A method according to claim 1 wherein said processing determines the direction of motion of at least one point.

10. A method according to claim 1 wherein said determined variable is compared to a norm.

11. A method according to claim 1 wherein said determined variable is used to diagnose a condition of said person.

12. A method according to claim 1 wherein said determined variable is used to determine the quality of movement of said person.

13. A method according to claim 1 wherein said display provides information concerning activity of persons located remotely.

14. A method according to claim 1 wherein said display provides information concerning said person's goals or prior performance.

15. A method according to claim 1 wherein said determined variable is used in said program.

16. A method according to claim 1 wherein said video game is designed to allow reliable sensing of said points while undertaking said game.

17. A computer based exercise method comprising the steps of:
- providing an exercise machine on which a person exercises;
- providing a first computer to run a video game on a video display;
- electro-optically determining data concerning a plurality of points on at least one of said person and said machine;
- processing said data to determine a variable related to one or more of said points; and
- using said determined variable, controlling a video game program using said first computer, wherein said processing is performed by a second computer different than the first computer that is used to run said video game.

18. A computer based exercise method comprising the steps of:
- providing an exercise machine on which a person exercises;
- providing a computer and a computer-controlled video display for viewing by said person and defining a long axis, wherein the long axis of said display is substantially vertical;
- electro-optically determining data concerning a plurality of points on at least one of said person and said machine;
- processing said data to determine a variable related to one or more of said points; and
- using said determined variable, controlling a video game program in said computer.

19. An exercise system comprising:
- an exercise machine, said exercise machine resisting the effort of a person when said person is exercising;
- a video display for viewing by said person exercising on said machine;
- a video game console running a video game program providing video game related images on said display;
- at least one electro-optical sensor viewing a plurality of points on at least one of said person and said machine;
- a computer to process information from said sensor and determine a variable concerning said plurality of points; and
- an interface from said computer to said game console.

20. Apparatus according to claim 19 wherein said sensor is a TV camera.

21. Apparatus according to claim 19 wherein said exercise machine is a bicycle.

22. An exercise system comprising:
- an exercise machine adapted to resist the effort of a person when the person is exercising;
- a video display viewable by the person when the person is exercising in conjunction with the exercise machine;
- an electro-optical sensor including a field of view encompassing a plurality of points on at least one of the person and the exercise machine, the electro-optical sensor having an output;
- a computer responsive to the electro-optical sensor output, the computer being adapted to control the video display based on the electro-optically observed points of at least one of the person and the exercise machine while exercising; and
- a microphone having an output coupled to the computer.

23. An exercise system comprising:
- an exercise machine adapted to resist the effort of a person when the person is exercising;
- a video display viewable by the person when the person is exercising in conjunction with the exercise machine;
- an electro-optical sensor including a field of view encompassing a plurality of points on at least one of the person and the exercise machine, the electro-optical sensor having an output, wherein the electro-optical sensor includes a video camera;
- a computer responsive to the electro-optical sensor output, the computer being adapted to control the video display based on the electro-optically observed points of at least one of the person and the exercise machine while exercising.

* * * * *